United States Patent
Gong et al.

(10) Patent No.: US 11,712,434 B2
(45) Date of Patent: Aug. 1, 2023

(54) COMPOUND HAVING ANTI-CANCER EFFECT, AND PREPARATION METHOD THEREFOR AND USE THEREOF

(71) Applicant: 3D MEDICINES (BEIJING) CO., LTD., BDA Bejing (CN)

(72) Inventors: John Gong, BDA Bejing (CN); Yihui Lin, BDA Bejing (CN); Fengqing Li, BDA Bejing (CN); Fangqiang Tang, BDA Bejing (CN)

(73) Assignee: 3D MEDICINES (BEIJING) CO., LTD., BDA Beijing (CN)

( * ) Notice: Subject to any disclaimer, the term of this patent is extended or adjusted under 35 U.S.C. 154(b) by 447 days.

(21) Appl. No.: 16/461,842

(22) PCT Filed: Nov. 17, 2017

(86) PCT No.: PCT/CN2017/111649
§ 371 (c)(1),
(2) Date: May 17, 2019

(87) PCT Pub. No.: WO2018/090974
PCT Pub. Date: May 24, 2018

(65) Prior Publication Data
US 2019/0365711 A1     Dec. 5, 2019

(30) Foreign Application Priority Data
Nov. 17, 2016    (CN) .......................... 201611027194.X

(51) Int. Cl.
*A61K 31/416* (2006.01)
*A61P 35/00* (2006.01)
*C07D 231/56* (2006.01)

(52) U.S. Cl.
CPC ............ *A61K 31/416* (2013.01); *A61P 35/00* (2018.01); *C07D 231/56* (2013.01)

(58) Field of Classification Search
CPC ...... A61K 31/416; A61P 35/00; C07D 231/56
See application file for complete search history.

(56) References Cited

FOREIGN PATENT DOCUMENTS

WO    2014201127    12/2014

OTHER PUBLICATIONS

Chong Toh et al. Cancer (2015), vol. 119, pp. 380-387 (Year: 2015).*

* cited by examiner

*Primary Examiner* — Samira J Jean-Louis
(74) *Attorney, Agent, or Firm* — Grogan, Tuccillo & Vanderleeden, LLP

(57) ABSTRACT

The present invention provides a compound of the formula I, a process for its preparation and the use of a medicament for the treatment of cancer. The compound of the present invention has an inhibitory effect on various cancer cells and can be biologically converted into the active drug Linifanib in vitro (in plasma) to inhibit the proliferation of tumor cells, especially liver cancer cells, at a lower dose.

9 Claims, No Drawings

COMPOUND HAVING ANTI-CANCER EFFECT, AND PREPARATION METHOD THEREFOR AND USE THEREOF

CROSS REFERENCE TO RELATED APPLICATIONS

This is a national stage application under 35 U.S.C. § 371 (c) of prior-filed, co-pending, PCT application serial number PCT/CN2017/111649, filed on Nov. 17, 2017, which claims priority to Chinese patent application number 201611027194.X, filed Nov. 17, 2016, the entire contents of which are incorporated herein in their entireties.

TECHNICAL FIELD

The invention relates to a compound and a preparation method and application thereof, in particular, to a compound which can be selectively converted in vivo to have a stronger anticancer activity, and a preparation method and application thereof.

BACKGROUND

Using anti-tumor drugs to selectively kill tumor cells with less toxicity to normal cells has been a difficulty problem in tumor therapy. In recent years, the targeted therapy focusing on the mutation of specific targets in tumor cells has brought hope to cancer patients. However, targeted therapy also has many limitations such as a small population of beneficiary patients and rapid drug resistance after administration. New biomedical research and development taking a different approach to provide new treatment options for more patients is needed.

Linifanib is a multi-target anticancer compound which targets mostly angiogenesis-related kinase, and has good inhibitory effects on VEGFr, PDGFRs, CDF-1R and Flt-1/3. In a large randomized phase III clinical trial of liver cancer, Linifanib was found to be superior to the sole approved targeted drug Sorafenib in live cancer in parameters such as TTP (time to progression) and ORR (overall response rate) in liver cancer patients (TTP: 5.4 months vs. 4.0 months, ORR 13.0% vs. 6.9%). However, its toxicity and side effects are also greater than Sorafenib, thus, the overall efficacy is not stronger than Sorafenib, and therefore did not obtain FDA approval (J. Clin. Oncol., 2014, 33, 172-179).

DESCRIPTION OF INVENTION

In order to solve the above problems, the present application binds Linifanib or a derivative thereof to a polypeptide through a multi-carbon chain to form a compound Linifanib-Cx-AAy (i.e., a compound of formula I of the present invention); utilizing the high expression of PSMA (Prostate-Specific Membrane Antigen) in the tumor endothelial cells in solid tumors and in some tumor cells, specifically degrading Linifanib-Cx-AAy at the tumor site to form active anticancer compound Linifanib or its derivatives, therefore, the anti-cancer compound is specifically accumulated at the tumor site while reducing its systemic toxicity.

One aspect of the present application provides a compound having the structure of Formula I, a pharmaceutically acceptable salt, stereoisomer, solvate, or polymorph thereof:

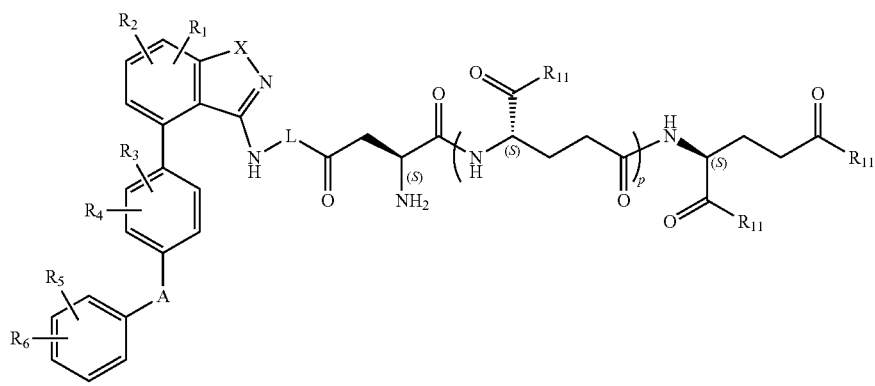

Formula I wherein,

X is selected from the group consisting of O, S and $NR_9$;

A is selected from $(CH_2)eN(R_7)C(O)N(R_8)(CH_2)f$ and $CH_2C(O)NR_7$, wherein e and f are independently 0 or 1, wherein each group is bonded from its left to rings substituted by R3 and R4;

L is —[Cm(O)(Z)n(NH)q]-, where m, q are 0 or 1, n is 0-11, p is 0-8; Z is a group or several groups connected in the usual way from —$CR_{10}$—, —$CR_{10}$—O—$CR_{10}$, —S—S—, —$CR_{10}$=$CR_{10}$—, —$CR_{10}$≡$CR_{10}$—, —Ar, —CO—NH— and —N=$CR_{10}$—;

R1 and R2 are independently selected from the group consisting of hydrogen, alkoxy, alkoxyalkoxy, alkoxyalkyl, alkyl, aryloxy, aryloxyalkyl, halo, haloalkoxy, haloalkyl, heterocycle, heterocyclylalkenyl, heterocyclylalkoxy, heterocyclylalkyl, heterocyclyloxyalkyl, hydroxy, hydroxyalkoxy, hydroxyalkyl, (NRaRb)alkoxy, (NRaRb) Alkenyl, (NRaRb)alkyl, (NRaRb)carbonylalkenyl and (NRaRb)carbonylalkyl;

R3 and R4 are independently selected from the group consisting of hydrogen, alkoxy, alkyl, halo, haloalkoxy, haloalkyl and hydroxy;

R5 and R6 are independently selected from the group consisting of hydrogen, alkoxy, alkoxyalkyl, alkoxycarbonyl, alkyl, aryloxy, arylalkyl, carboxy, cyano, halo, haloalkoxy, haloalkyl, Hydroxy, hydroxyalkyl, nitro and —NRcRd;

$R_7$ and $R_8$ are independently selected from the group consisting of hydrogen and alkyl;

$R_9$ is selected from the group consisting of hydrogen, alkenyl, alkoxyalkyl, alkyl, alkoxycarbonyl, aryl, heterocyclylalkyl, hydroxyalkyl and (NRaRb)alkyl;

$R_{10}$ is selected from the group consisting of hydrogen, alkyl, alkoxy, aryloxy, alkenyloxy, nitro, halo, primary, secondary and tertiary amine;

$R_{11}$ is selected from the group consisting of hydrogen, hydroxy, amino, alkenyl, alkynyl, alkoxy, alkylamino, alkokyalkyl, alkyl, alkoxycarbonyl, aryl, heterocycloalkyl;

Ra and Rb are independently selected from the group consisting of hydrogen, alkyl, alkylcarbonyl, alkyl sulfonyl, aryl sulfonyl, haloalkylsulfonyl and heterocyclylsulfonyl;

Rc and Rd are independently selected from the group consisting of hydrogen, alkyl, alkylcarbonyl, aryl, arylalkyl, cycloalkyl, cycloalkylalkyl, heterocyclyl and heterocyclylalkyl.

Specifically, the structure of each compound is shown as follows:

| Number | Compound |
|---|---|
| 1 | 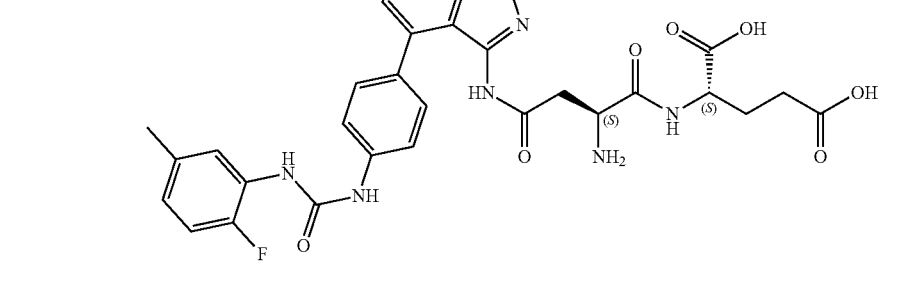 |
| 2 | 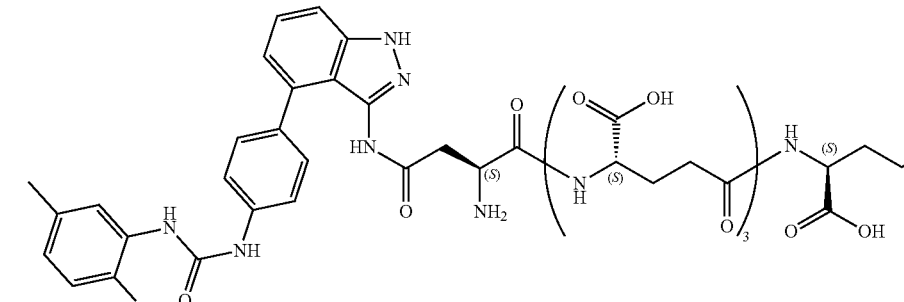 |
| 3 | 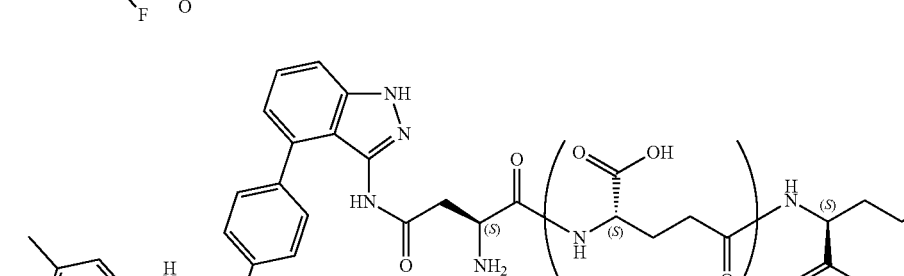 |
| 4 | 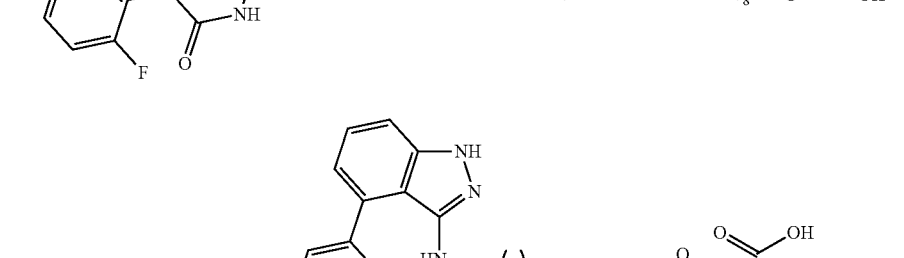 |

| Number | Compound |
|---|---|
| 5 | 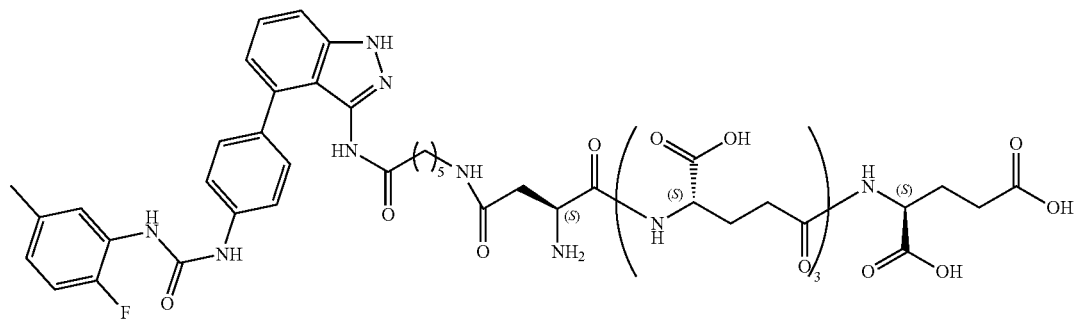 |
| 6 | 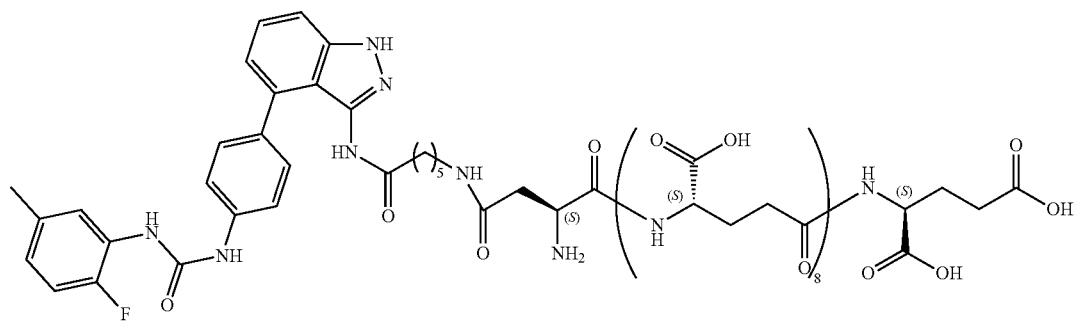 |
| 7 | 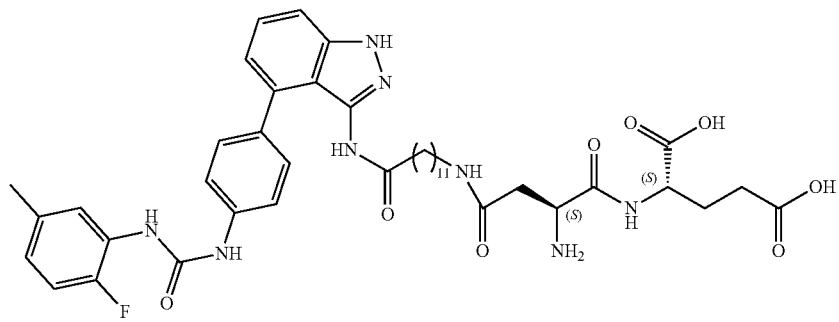 |
| 8 (Linifanib-C₁₂-AA₅) | 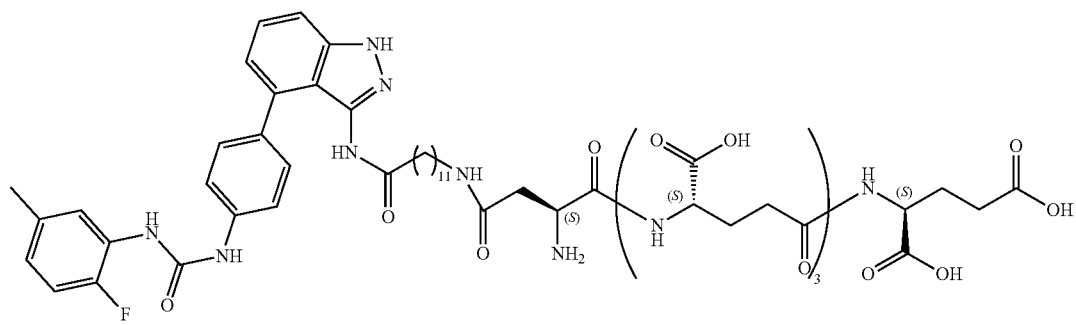 |

| Number | Compound |
|---|---|
| 9 | 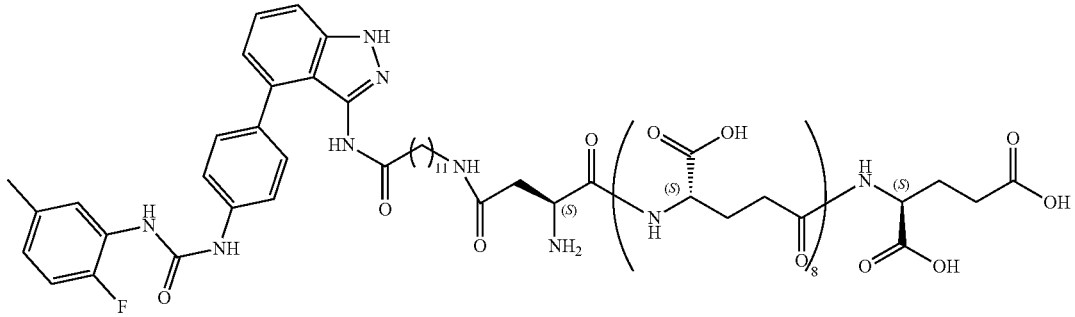 |

Reaction Route:

First, the polypeptide (reactant 1) and the benzyl-protected L (reactant 2) are reacted in the presence of a catalyst and a condensing agent to obtain a protected group-containing intermediate compound 1, which is further catalyze and hydrogenated in a polar solvent to remove the protecting group to obtain intermediate compound 2;

The intermediate compound 2 is reacted with Linifanib or a derivative thereof in the presence of a catalyst and a condensing agent to obtain a protecting group-containing intermediate compound 3, which further undergoes acidic conditions to remove the protecting group to obtain a compound of formula I.

Map of Reaction Route:

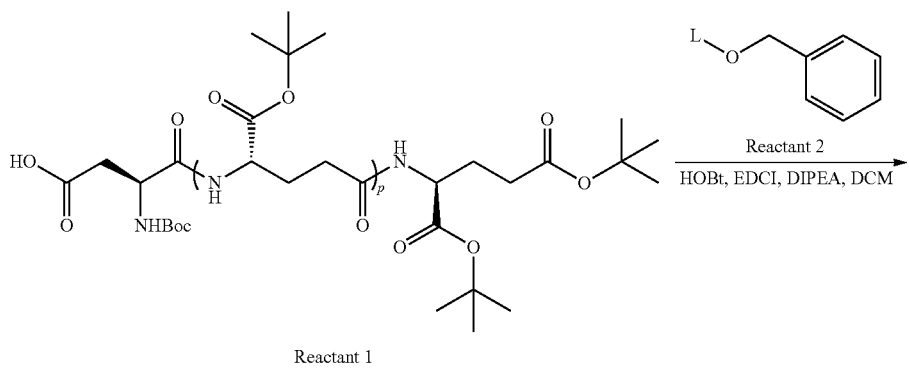

Reactant 1

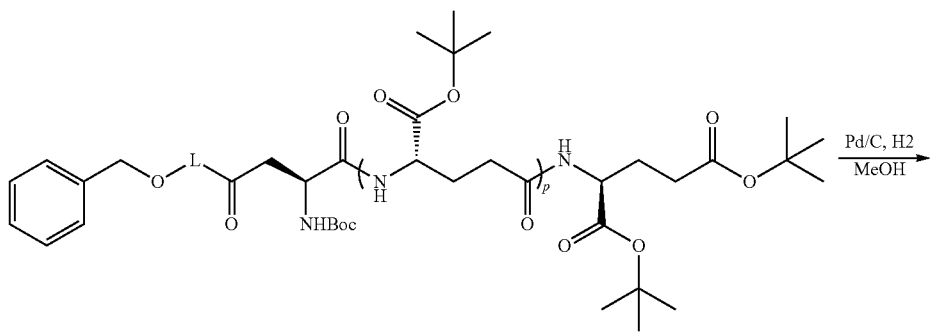

Intermediate compound 1

-continued
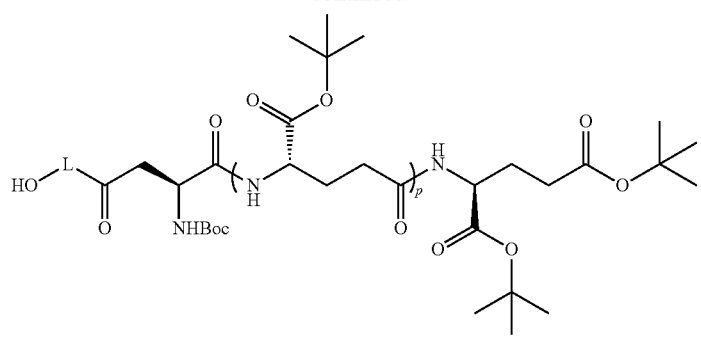
Intermediate compound 2
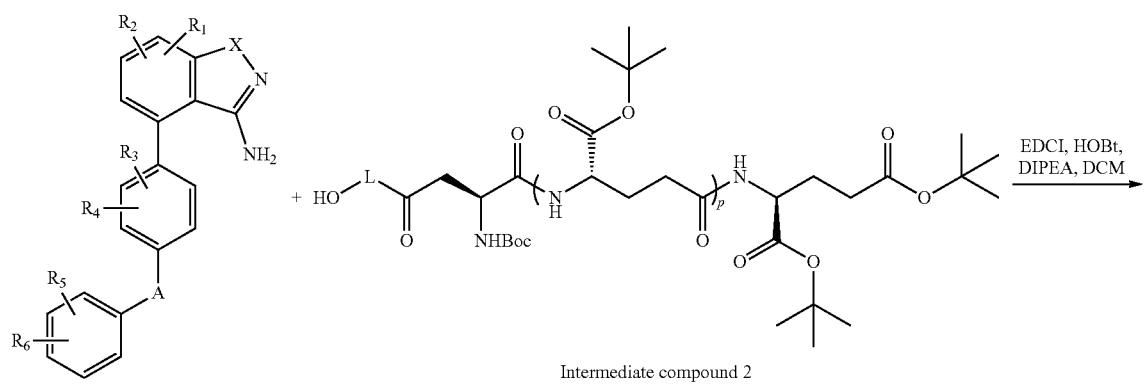
Linifanib or its derivatives    Intermediate compound 2
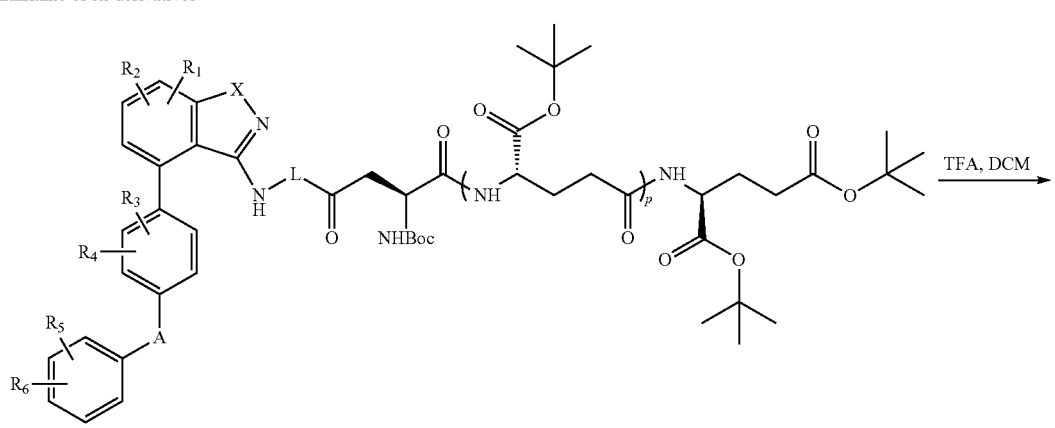
Intermediate compound 3
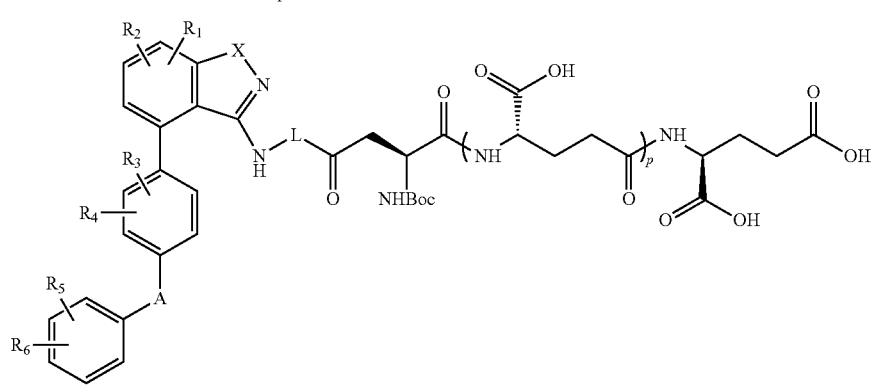
Formula I Compound Furthermore, in the above method for preparing the intermediate compound 1, the reaction temperature is carried out at −20° C. to 125° C.; the organic solvent is selected from the group consisting of ethers, alcohols, alkanes, aromatic hydrocarbons having 1 to 20 carbon atoms a ketone, an alkyl halide, an amide, a nitrile, an ester or a mixture thereof; the catalyst is 1-hydroxybenzotriazole (HOBT); the condensing agent is selected from any one or more from 1-ethyl-3-(3-dimethylaminopropyl), carbodiimide hydrochloride (EDCl), 1,3-dicyclohexylcarbodiimide (DCC) or 4-dimethylaminopyridine (DMAP). In this step, the molar ratio of the reactants 1 and 2 in the reaction is 1:1 to 1:10, and the molar ratio of the reactant 1 to the condensing agent is 1:0.1 to 1:10; the molar ratio of the reactant 1 to the catalyst is 1:0.1 to 1:10.

Furthermore, in the above process for preparing the intermediate compound 2, the reaction temperature is carried out at −20° C. to 250° C.; the organic solvent is selected from the group consisting of ethers, alcohols, alkyl halides, amides, nitriles or mixtures thereof having from 1 to 20 carbon atoms, or a mixture with water in various ratios; the catalyst is palladium carbon, palladium hydroxide of dry or wet form. In the above preparation method, the molar ratio of the intermediate compound 2 to the catalyst is from 1:0.1 to 1:10.

Furthermore, in the above method for preparing the intermediate compound 3, the above reaction temperature is carried out at −20° C. to 125° C.; the organic solvent is selected from the group consisting of ethers, alcohols, alkanes, aromatic hydrocarbons, ketones, alkyl halides, amides, nitriles, esters, or a mixture thereof having from 1 to 20 carbon atoms; the catalyst is 1-hydroxybenzotriazole (HOBT); the condensing agent is any one or more of 1-ethyl-3-(3-dimethylaminopropyl) carbon diimine hydrochloride (EDCl), 1,3-dicyclohexylcarbodiimide (DCC) or 4-dimethylaminopyridine (DMAP). In this step, the molar ratio of Linifanib or its derivative to intermediate compound 2 is 1:1 to 1:10, the molar ratio of Linifanib or its derivative to condensing agent is 1:0.1 to 1:10, and the molar ratio to catalyst is 1:0.1 to 1:10.

Furthermore, in the above method for preparing the compound of the formula 1, the reaction temperature is carried out at −20° C. to 125° C.; the organic solvent is an ether, an alcohol, an alkane, an aromatic hydrocarbon, a ketone, a halogenated alkane, an amide, a nitrile, an ester or a mixture thereof in various ratios having from 1 to 20 carbon atoms; the acidic reagent is formic acid, acetic acid, trifluoroacetic acid. In the above preparation method, the molar ratio of the intermediate compound 3 to the acidic reagent is 1:1 to 1:10.

Another aspect of the present application provides a medicament prepared from an active ingredient and a pharmaceutically acceptable carrier, wherein the active ingredient is a compound of Formula I, a pharmaceutically acceptable salt thereof, stereoisomers, solvates or polymorphs. Such drugs include, but are not limited to, oral dosage forms, parenteral dosage forms, topical dosage forms, and rectal administration dosage forms. In some embodiments, the medicament may be an oral tablet, a capsule, a pill, a powder, a sustained release preparation, a solution and a suspension; a sterile solution, suspension or emulsion for parenteral injection; a topical ointment or cream; or a suppository for rectal administration. In some embodiments, the drug and at least one therapeutic agent are each combined in a separate dosage form into a combined product, such as a kit.

Another aspect of the present application provides a pharmaceutical composition comprising a compound of the above Formula I, or a pharmaceutically acceptable salt, stereoisomer, solvate, polymorph thereof, and a pharmaceutically acceptable carrier according to the present application. The pharmaceutical compositions include, but are not limited to, oral dosage forms, parenteral dosage forms, topical dosage forms, and rectal administration dosage forms. In some embodiments, the pharmaceutical composition may be an oral tablet, capsule, pill, powder, sustained release preparation, solution and suspension; sterile solution, suspension or emulsion for parenteral injection; an ointment or cream for topical use; or a suppository for rectal administration. In some embodiments, the pharmaceutical composition and the at least one therapeutic agent are each combined in a separate dosage form into a combined product, such as a kit.

Another aspect of the present application provides the use of a compound of formula I, a pharmaceutically acceptable salt, stereoisomer, solvate, polymorph thereof, for the manufacture of a medicament having anticancer effects. The cancer includes esophageal cancer, endometrial cancer, malignant lymphoma, multiple myeloma, gastrointestinal stromal tumor, colon cancer, rectal cancer, breast cancer, liver cancer, stomach cancer, ovarian cancer, uterine cancer, cervical cancer, Vaginal cancer, lung cancer, kidney cancer, prostate cancer, bladder cancer, pancreatic cancer, brain cancer, melanoma, etc. Preferably, the effect is optimal for liver cancer.

Another aspect of the present application provides a method of treating cancer comprising administering a therapeutically effective amount of a compound of formula I, a pharmaceutically acceptable salt, stereoisomer, solvate, polymorph thereof to individuals with the need. In some examples, the cancer comprises esophageal cancer, endometrial cancer, malignant lymphoma, multiple myeloma, gastrointestinal stromal tumor, colon cancer, rectal cancer, breast cancer, liver cancer, gastric cancer, ovarian cancer, Uterine cancer, cervical cancer, vaginal cancer, lung cancer, kidney cancer, prostate cancer, bladder cancer, pancreatic cancer, brain cancer, melanoma, etc. Preferably, the effect is optimal for liver cancer.

As used herein, "pharmaceutically acceptable salt" refers to a salt that retains the biological effectiveness of the free acid and free base of the specified compound, and which has no adverse effects biologically or otherwise. The salt in the present application means an acid salt formed with an organic acid/inorganic acid, and a basic salt formed with an organic base/inorganic base.

As used herein, "solvate" refers to a combination of a compound of the present application and a solvent molecule formed by solvation. Such as hydrates, ethanol solvates, methanol solvates, and the like.

As used herein, "polymorphs" or "polymorph" refers to a compound of the present application that exists in a different lattice form.

As used herein, "stereoisomer" refers to isomers resulting from the different arrangement of atoms in a molecule in space.

As used herein, "pharmaceutical composition" refers to a biologically active compound optionally mixed with at least one pharmaceutically acceptable chemical component including, but not limited to, carriers, stabilizers, diluents, dispersing agents, suspending agents, thickening agents and/or excipients. The "carrier" refers to a relatively non-toxic chemical agent that facilitates the introduction of a compound into a cell or tissue. As used herein, "alkyl" refers to a straight or branched saturated hydrocarbon chain containing from 1 to 10 carbon atoms, including but not limited to methyl, ethyl, n-propyl, isopropyl, n-butyl, Sec-butyl, isobutyl, tert-butyl, n-pentyl, isopentyl, neopentyl, n-hexyl, 3-methylhexyl, 2,2-dimethylpentyl, 2,3-dimethyl Amyl, n-heptyl, n-octyl, n-decyl and n-decyl.

The "aryl group" means an aromatic carbocyclic group having 6 to 14 carbon ring atoms. The aryl group can be monocyclic or polycyclic. In the case of a polycyclic aromatic ring, only one of the polycyclic systems needs to be unsaturated, while the remaining one or more rings may be saturated, partially saturated or unsaturated. Examples of the aryl group include a phenyl group, a naphthyl group, an anthracenyl group, an indanyl group, and a tetrahydronaphthyl group.

The "heteroaryl" refers to a five- or six-membered aromatic ring having at least one carbon atom and one or more independently selected nitrogen, oxygen or sulfur atoms. Specifically, the "heteroaryl group" means an aromatic heterocyclic group having 5 to 14 ring atoms. The heteroaryl group can be a single ring or two or three fused rings. Examples of heteroaryl substituents include: 6-membered ring substituents such as pyridyl, pyrazinyl, pyrimidinyl, pyridazinyl and 1,3,5-, 1,2,4- or 1,2,3-triazinyl; 5-membered ring substituent such as imidazolyl, furyl, thienyl, pyrazolyl, oxazolyl, isoxazolyl, thiazolyl, 1,2,3-, 1,2,4-, 1,2,5-, or 1,3, 4-oxadiazolyl and isothiazolyl; 6/5-membered fused ring substituents such as benzothienyl, benzisoxazolyl, benzoxazole Base, imidazolyl, fluorenyl, benzimidazolyl, pyrrolo[2, 3-b]pyridinyl, fluorenyl; and 6/6-membered fused ring, such as benzopyranyl, quinolyl, isoquinolinyl, porphyrinyl, quinazolinyl and benzoxazinyl.

The "cycloalkenyl" refers to a monocyclic or bridged hydrocarbon ring system. The monocyclic cycloalkenyl group has 4, 5, 6, 7 or 8 carbon atoms and 0 heteroatoms. The four-membered ring system has one double bond, and the five- or six-membered ring system has one or two double bonds, and the seven- or eight-membered ring system has one, two or three double bonds. Representative examples of monocyclic cycloalkenyl include, but are not limited to, cyclobutenyl, cyclopentenyl, cyclohexenyl, cycloheptenyl, and cyclooctenyl.

The "heterocycloalkyl group" means a saturated ring structure containing a total of 3 to 14 ring atoms. At least one of the ring atoms is a hetero atom (i.e., oxygen, nitrogen or sulfur), and the remaining ring atoms are independently selected from the group consisting of carbon, oxygen, nitrogen and sulfur, such as tetrahydrofuranyl, tetrahydropyranyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl.

The term "effective amount" is meant a non-toxic, but sufficient amount of a drug or agent that provides the desired effect. In the pharmaceutical compositions or kits of the invention, an "effective amount" of an ingredient or formulation unit refers to an amount of the ingredient that is effective to provide the desired effect when used in combination with other ingredients. The "effective amount" will vary from subject to subject, depending on the age and general condition of the individual, the specific active drug, and the like. Thus, it is not always possible to refer to an accurate "effective amount", however, a suitable "effective amount" in any individual case can be determined by one of ordinary skill in the art using routine experimental methods.

The term "subject" can refer to a patient or other animal, particularly a mammal, such as a human, a dog, a monkey, a cow, a horse, etc., that receives a compound or pharmaceutical composition of the invention to treat, prevent, ameliorate, and/or alleviate the disease of the invention.

For in vitro experiments, the present application also synthesizes a metabolite of a compound of Formula I, a compound of Formula II, in the reaction route is as follows:

First, Linifanib or its derivative is reacted with Boc-protected L (Reactant 3) under the conditions of a condensing agent and a catalyst to form an intermediate compound Ma, which is under the action of trifluoroacetic acid to remove Boc protection to obtain Intermediate compound Mb; the intermediate compound Mb is further condensed with a protecting group of aspartic acid to obtain an intermediate compound Mc, and the intermediate compound Mc is under the trifluoroacetic acid condition to remove the Boc protection to form an intermediate compound Md, intermediate compound Md is catalyzed and hydrogenated under a noble metal catalyst condition to remove the benzyl group to obtain the metabolite of the compound of formula 2.

Map of Reaction Route:

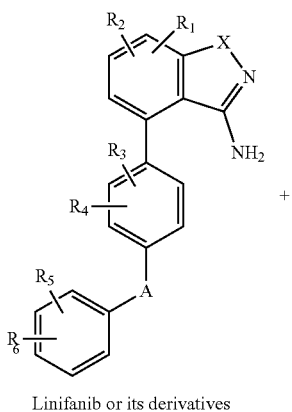

Linifanib or its derivatives

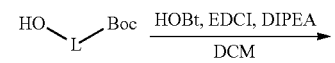

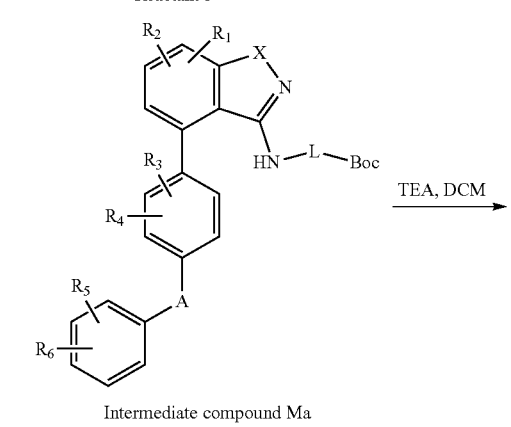

Intermediate compound Ma

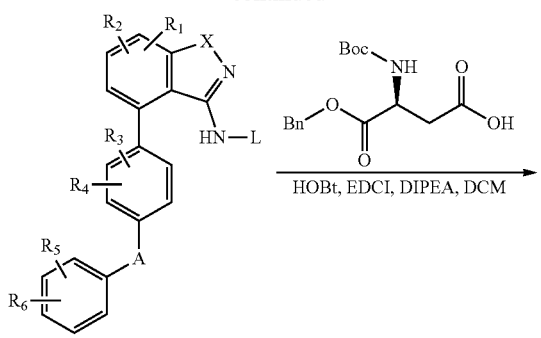

Intermediate compound Mb

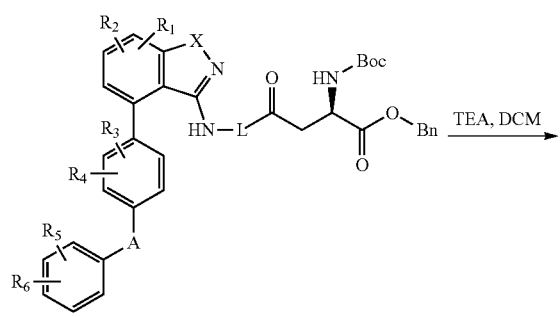

Intermediate compound Mc

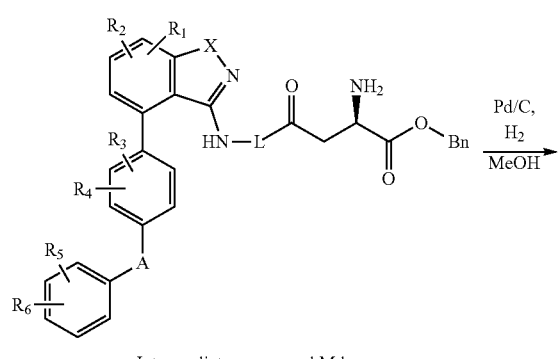

Intermediate compound Md

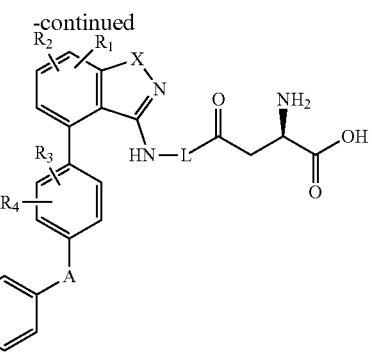

Formula II compound wherein,

X is selected from the group consisting of O, S and NR$_9$;

A is selected from (CH$_2$)eN(R$_7$)C(O)N(R$_8$)(CH$_2$)f and CH$_2$C(O)NR$_7$, wherein e and f are independently 0 or 1, wherein each group is bonded from its left to rings substituted by R3 and R4;

L is —[Cm(O)(Z)n(NH)q]-, where m, q are 0 or 1, n is 0-11, p is 0-8; Z is a group or several groups connected in the usual way from —CR$_{10}$—, —CR$_{10}$—O—CR$_{10}$—, —S—S—, —CR$_{10}$=CR$_{10}$—, —CR$_{10}$≡CR$_{10}$—, —Ar, —CO—NH— and —N=CR$_{10}$—;

R1 and R2 are independently selected from the group consisting of hydrogen, alkoxy, alkoxyalkoxy, alkoxyalkyl, alkyl, aryloxy, aryloxyalkyl, halo, haloalkoxy, haloalkyl, heterocycle, heterocyclylalkenyl, heterocyclylalkoxy, heterocyclylalkyl, heterocyclyloxyalkyl, hydroxy, hydroxyalkoxy, hydroxyalkyl, (NRaRb)alkoxy, (NRaRb) Alkenyl, (NRaRb)alkyl, (NRaRb)carbonylalkenyl and (NRaRb)carbonylalkyl;

R3 and R4 are independently selected from the group consisting of hydrogen, alkoxy, alkyl, halo, haloalkoxy, haloalkyl and hydroxy;

R5 and R6 are independently selected from the group consisting of hydrogen, alkoxy, alkoxyalkyl, alkoxycarbonyl, alkyl, aryloxy, arylalkyl, carboxy, cyano, halo, haloalkoxy, haloalkyl, Hydroxy, hydroxyalkyl, nitro and —NRcRd;

R$_7$ and R$_8$ are independently selected from the group consisting of hydrogen and alkyl;

R9 is selected from the group consisting of hydrogen, alkenyl, alkoxyalkyl, alkyl, alkoxycarbonyl, aryl, heterocyclylalkyl, hydroxyalkyl and (NRaRb)alkyl;

R$_{10}$ is selected from the group consisting of hydrogen, alkyl, alkoxy, aryloxy, alkenyloxy, nitro, halo, primary, secondary and tertiary amine;

Ra and Rb are independently selected from the group consisting of hydrogen, alkyl, alkylcarbonyl, alkylsulfonyl, arylsulfonyl, haloalkylsulfonyl and heterocyclylsulfonyl;

Rc and Rd are independently selected from the group consisting of hydrogen, alkyl, alkylcarbonyl, aryl, arylalkyl, cycloalkyl, cycloalkylalkyl, heterocyclyl and heterocyclylalkyl.

Specifically, the structure of each compound is shown as follows:

| Number | Compound |
|---|---|
| 10 | |
| 11 | |
| 12 Linifanib-C$_{12}$-Asp | |

The present invention shows that the compound of Formula I has an inhibitory effect on various cancer cells and can be biologically converted into the active drug Linifanib in plasma in vitro to inhibit the proliferation of tumor cells, especially liver cancer cells, at a lower dose.

EXAMPLES

Examples 1 and 2: Preparation of Target Compound 1

Example 1 Preparation of Intermediate Compound 3

Weighed and took 760 mg (1.6 mmol) 1-N Boc Linifanib, 324 mg of HOBT (2.4 mmol), and 460 mg of EDCl (2.4 mmol) to dissolve in 50 ml of dichloromethane, stirred and reacted for 0.5 h, controlling reaction temperature at 20~40° C. and slowly added 912 mg of the intermediates compound 2 Asp (BOC)-Glu (OtBu)-(OtBu) (1.92 mmol) which is available in market, and finally added 516 mg of DIPEA (4.0 mmol); maintaining the reaction temperature and stirring reacting for 12 h. TLC (DCM/MeOH=40:1) detected a complete reaction. 100 ml of dichloromethane was added to dilute the reaction solution, and the solution was washed with 250 ml deionized water twice. The organic phase was then washed with 150 ml saturated sodium solution, and the organic phase was dried with anhydrous sodium sulfate. Desiccant was filtered and concentrated at low temperature to obtain a brown oily object. The oily object was carried out by Silica Gel column chromatography (DCM:MeOH=0:1100:1), and 498 mg of a white solid powder was obtain, with a yield rate of 33.4%.

Example 2 Preparation of Target Compound 1

Weighed and took 354 mg (0.38 mmol) of the intermediate Compound 3 prepared in Example 1 to dissolve in 20 ml dichloromethane, the reaction temperature was controlled at −5~5° C. Slowly added 3 ml of trifluoroacetate (0.04 mmol), and the reaction temperature was maintained and stir-reacted for 20~24 H; TLC (DCM/MeOH=40:1) detected a complete reaction. Added 40 ml of dichloromethane to dilute to the reaction solution, washed two times with 120 ml of deionized water, then wash two times with 60 ml of 5% sodium bicarbonate solution, and then washed two times with 120 ml of deionized water. Organic phase was separated and dried with anhydrous sodium sulfate. Desiccant was filtered and concentrated at low temperature to obtain a reddish-brown oily object. The oily object was prepared by chromatographic separation, and 88 mg of a white solid powder was obtained with a yield rate of 37.2%. HPLC purity: 94.1% (214 nm), 94.8% (254 nm). MS (ESI): m/z 620.0 [M+1]$^+$ The chemical structure is:

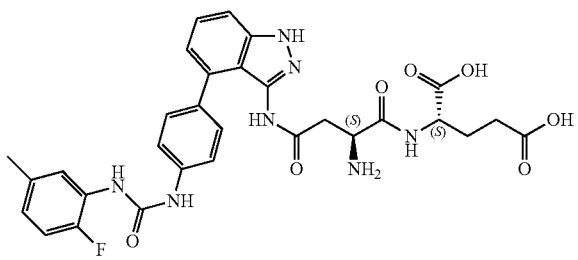

Examples 3-4: Preparation of Target Compound 2

Example 3 Preparation of Intermediate Compound 3

Weighed and took 760 mg (1.6 mmol) of 1-N Boc Linifanib, 324 mg of HOBT (2.4 mmol) and 460 mg of EDCl (2.4 mmol) to dissolve in 50 ml of dichloromethane and stir-reacted for 0.5 h, and controlled the reaction temperature at 20~40° C. slowly added 1978 mg of Intermediate compound 2 Asp(Boc)-Glu(OtBu)-Glu(OtBu)-Glu(OtBu)-Glu(OtBu)-(OtBu) (1.92 mmol) which is available in market, and finally added 516 mg of DIPEA (4.0 mmol). The reaction temperature was maintained and stir-reacted for 12 h, and TLC (DCM/MeOH=40:1) detected the completion of reaction. The reaction solution was diluted with 100 ml of dichloromethane, washed twice with 250 ml of deionized water, and the organic phase was separated. The organic phase was washed with 150 ml of saturated sodium solution and separated. The desiccant was filtered off and the filtrate was concentrated at low temperature to give a brown oily object. The oily object was subjected to silica gel column chromatography (DCM:MeOH=0:1 to 100:1) to give 588 mg of white solid powder, and the yield rate was 24.7%.

Example 4 Preparation of Target Compound 2

565 mg (0.38 mmol) of the intermediate compound 3 prepared in Example 3 was weighed and took to dissolve in 20 ml of dichloromethane, and the reaction temperature was controlled at −5 to 5° C., and 3 ml (0.04 mmol) of trifluoroacetic acid was slowly added to maintain the reaction temperature. The reaction was stirred for 20-24 h, and the reaction was complete by TLC (DCM/MeOH=40:1). The reaction solution was diluted with 40 ml of dichloromethane, washed twice with 120 ml of deionized water, twice with 60 ml of 5% sodium hydrogen carbonate solution, and twice with 120 ml of deionized water. The organic phase was separated, and the organic phase was dried over anhydrous sodium sulfate. The desiccant was filtered off and the filtrate was concentrated at low temperature to give a red brown oily object. The oily object was subjected to chromatography to give 129 mg of white solid powder, and the yield rate as 33.8%. HPLC purity: 95.9% (214 nm), 96.5% (254 nm). MS (ESI): m/z 1007.0 [M+1]$^+$ The chemical structure is:

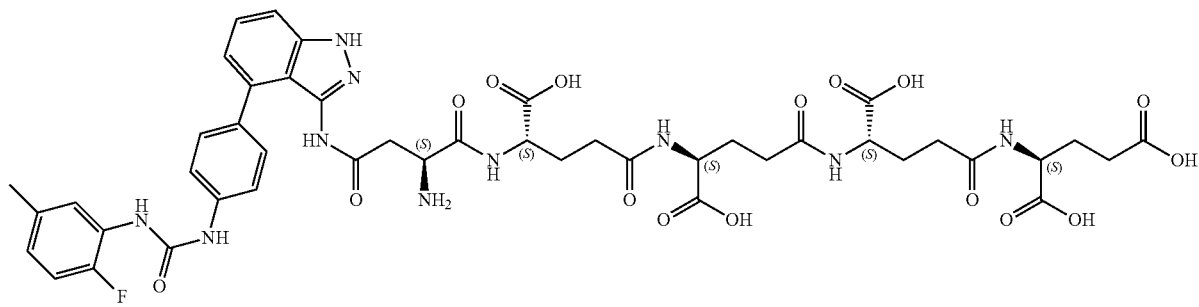

Examples 5-6: Preparation of Target Compound 3

Example 5 Preparation of Intermediate Compound 3

Weighed 760 mg (1.6 mmol) of 1-N Boc Linifanib, 324 mg of HOBT (2.4 mmol) and 460 mg of EDCl (2.4 mmol) to dissolve in 50 ml of dichloromethane, stir-reacted for 0.5 h, and controlled the reaction temperature at 20~40° C. Slowly added 3,756 mg of intermediate compound 2 Asp (Boc)-Glu(OtBu)-Glu(OtBu)-Glu(OtBu)-Glu(OtBu)-Glu (OtBu)-Glu(OtBu)-Glu(OtBu)-Glu(OtBu)-Glu (OtBu)-(OtBu) (1.92 mmol) which is available in market, and finally DIPEA 516 mg (4.0 mmol) was added, and the reaction was stirred for 12 h, and the reaction was completed by TLC (DCM/MeOH=40:1). The reaction solution was diluted with 100 ml of dichloromethane, washed twice with 250 ml of deionized water, and the organic phase was separated. The organic phase was washed with 150 ml of saturated sodium solution and separated. The desiccant was filtered off and the filtrate was concentrated at low temperature to give a brown oily object. The oily object was subjected to silica gel column chromatography (DCM:MeOH=0:1 to 100:1) to give 834 mg of white solid powder, with a yield rate of 21.6%.

Example 6 Preparation of Target Compound 3

917 mg (0.38 mmol) of the intermediate compound 3 prepared in Example 5 was weighed and dissolved in 20 ml of dichloromethane, and the reaction temperature was controlled at −5 to 5° C. 3 ml of trifluoroacetic acid (0.04 mmol)

was slowly added to maintain the reaction temperature. The reaction was stirred for 20-24 h, and the reaction was completed by TLC (DCM/MeOH=40:1). The reaction solution was diluted with 40 ml of dichloromethane, washed twice with 120 ml of deionized water, twice with 60 ml of 5% sodium hydrogen carbonate solution, and twice with 120 ml of deionized water. The organic phase was separated, and the organic phase was dried over anhydrous sodium sulfate. The desiccant was filtered off and the filtrate was concentrated at low temperature to give a red brown oily object. The oily object was subjected to chromatography to give 203 mg of a white solid powder, the yield rate was 32.4%. HPLC purity: 92.5% (214 nm), 94.1% (254 nm). MS (ESI): m/z 1652.0 [M+1]$^+$ Chemical structure is:

nitrogen atmosphere, and hydrogen was introduced and exchanged three times. The reaction was controlled at 2 MPa in the atmosphere, and the reaction was carried out at 20-65° C. for 6-12 h. The reaction was complete by TLC (DCM/MeOH=40:1). The reaction solution was filtered under nitrogen atmosphere to recover palladium carbon. The filtrate was concentrated at low temperature to give a yellow brown oily object. The oily object was subjected to chromatography to give 115 mg of pale-yellow solid powder, and yield rate was 46.6%.

Example 9 Preparation of Intermediate Compound 3

Weighed 760 mg (1.6 mmol) of 1-N Boc Linifanib, 324 mg of HOBT (2.4 mmol) and 460 mg of EDCl (2.4 mmol)

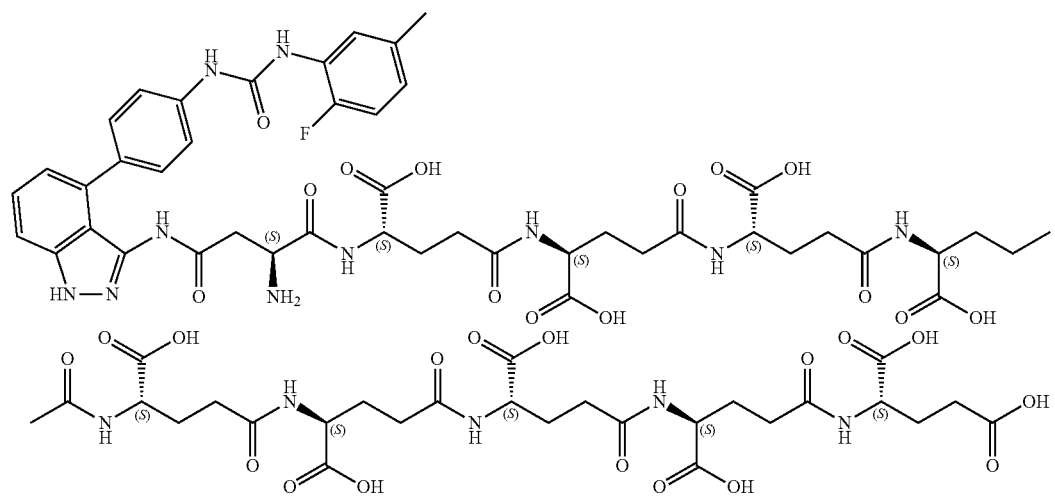

Examples 7-10: Preparation of Target Compound 4

Example 7 Preparation of Intermediate Compound 1

Weighed 304 mg of benzyl-(6-amino)hexaneate hydrochloride (1.18 mmol), 238 mg of HOBT (1.76 mmol) and 192 mg of EDCl 192 (1.76 mmol) to dissolve in 50 ml of dichloromethane, stirred at room temperature. Controlled reaction temperature at 2040° C. Slowly added 584 mg of Asp(Boc)-Glu(OtBu)-(OtBu) (1.23 mmol), maintained the reaction temperature, stir-reacted for 4 h, TLC (DCM/MeOH=40:1) detected the completion of the reaction. The reaction solution was diluted with 100 ml of dichloromethane, washed twice with 250 ml of deionized water, and the organic phase was separated. The organic phase was washed with 150 ml of saturated sodium solution and separated. The desiccant was filtered off and the filtrate was concentrated at low temperature to give a brown oily object. The oily object was subjected to silica gel column chromatography (petroleum ether/acetone=10:1 to 2:1) to yield 338 mg of a yellow solid powder; the yield rate was 42.3%.

Example 8 Preparation of Intermediate Compound 2

Weighed 285 mg of the intermediate compound 1 (0.42 mmol) prepared in Example 7 and dissolved in 60 ml of anhydrous methanol, and 10% Pd/C 25 mg was added under to dissolve in 50 ml of dichloromethane, stirred the reaction for 0.5 h, controlled the reaction temperature 2040° C. Slowly added 1129 mg of intermediate compound 2 (1.92 mmol) prepared in example 8 and finally DIPEA 516 mg (4.0 mmol) was added, and the reaction was stirred for 12 h, and the reaction was completed by TLC (DCM/MeOH=40:1). The reaction solution was diluted with 100 ml of dichloromethane, washed twice with 250 ml of deionized water, and the organic phase was separated. The organic phase was washed with 150 ml of saturated sodium solution, separated and dried with anhydrous sodium sulfate. The desiccant was filtered off and the filtrate was concentrated at low temperature to give a brown oily object. The oily object was subjected to silica gel column chromatography (DCM:MeOH=0:1 to 100:1) to give 579 mg of a white powder, and the yield rate was 34.6%.

Example 10 Preparation of Target Compound 4

Weighed 658 mg (0.63 mmol) of the intermediate compound 3 prepared in Example 9 to dissolve in 20 ml of dichloromethane, controlled the reaction temperature at −5~5° C. Slowly added 3 ml (0.04 mmol) of trifluoroacetic acid, maintained the reaction temperature. The reaction was stirred for 20-24 h, and the reaction was completed by TLC (DCM/MeOH=40:1). The reaction solution was diluted with 40 ml of dichloromethane, washed twice with 120 ml of deionized water, twice with 60 ml of 5% sodium hydrogen carbonate solution, and twice with 120 ml of deionized water. The organic phase was separated, and the organic phase was dried with anhydrous sodium sulfate. The desiccant was filtered off and the filtrate was concentrated at low temperature to give a red brown oily object. The oily object was subjected to chromatography to give 183 mg of a white solid powder, yield rate was 39.7%. $^1$HNMR (400 MHz, DMSO-d6) δ: 9.30 (s, 1H), 8.67 (d, J=7.6 Hz, 1H), 8.58 (d, J=2.0 Hz, 1H) 8.31 (d, J=8.0 Hz, 1H) 8.25-8.22 (m, 1H), 8.09 (s, 3H), 7.99 (d, J=6.4 Hz, 1H), 7.64-7.58 (m, 3H), 7.41 (d, J=8.4 Hz, 1H), 7.19-7.09 (m, 2H), 6.83 (d, J=5.6 Hz, 1H), 5.17 (s, 2H), 4.26-4.14 (m, 2H), 3.15-2.97 (m, 4H), 2.70-2.54 (m, 2H), 2.33-2.32 (m, 2H), 2.28 (s, 3H), 2.00-1.69 (m, 4H), 1.50-1.36 (m, 4H). HPLC purity: 98.2% (214 nm), 98.5% (254 nm). MS (ESI): m/z 733.0 [M+1]$^+$ The chemical structure is:

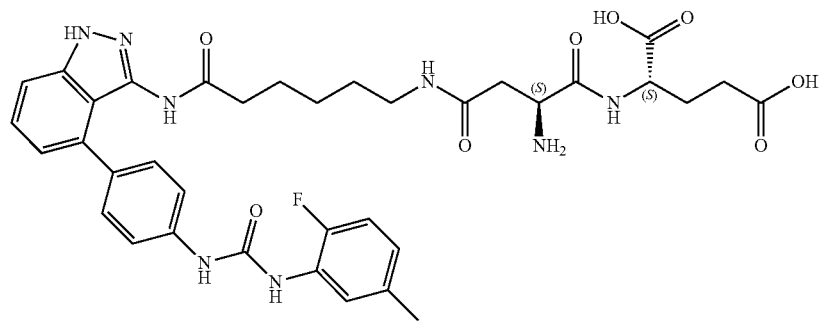

Examples 11-14: Preparation of Target Compound 5

Example 11 Preparation of Intermediate Compound 1

Weighed 304 mg of benzyl-(6-amino)hexaneate hydrochloride (1.18 mmol), 238 mg of HOBT (1.76 mmol) and 192 mg of EDCl (1.76 mmol) to dissolve in 50 ml of dichloromethane, stirred at room temperature. Controlled reaction temperature at 2040° C. Slowly added 1267 mg of Asp(Boc)-Glu(OtBu)-Glu(OtBu)-Glu(OtBu)-Glu(OtBu)-(OtBu) (1.23 mmol), and maintained the reaction temperature and stir-reacted for 4 h, and the reaction was completed by TLC (DCM/MeOH=40:1). The reaction solution was diluted with 100 ml of dichloromethane, washed twice with 250 ml of deionized water, and the organic phase was separated. The organic phase was washed with 150 ml of saturated sodium solution and separated. The organic phase was dried with anhydrous sodium sulfate. The desiccant was filtered off and the filtrate was concentrated at low temperature to give a brown oily object. The oil was subjected to silica gel column chromatography (peel ether/acetone=10:1 to 2:1) to yield 544 mg of a yellow solid powder. The yield rate was 37.4%.

Example 12 Preparation of Intermediate Compound 2

518 mg (0.42 mmol) of the intermediate compound 1 prepared in Example 11 was weighed and dissolved in 60 ml of anhydrous methanol, and 10% Pd/C 25 mg was added under nitrogen atmosphere, and hydrogen was introduced and exchanged for 3 times. The reaction was controlled at 2 MPa in the atmosphere, and the reaction was carried out at 20-65° C. for 6-12 h. The reaction was completed by TLC (DCM/MeOH=40:1). The reaction solution was filtered under nitrogen atmosphere to recover palladium carbon. The filtrate was concentrated at low temperature to give a yellow-brown oily object. The oily object was subjected to chromatography to give 244 mg of a pale-yellow solid powder, yield rate was 50.8%.

Example 13 Preparation of Intermediate Compound 3

Weighed 760 mg (1.6 mmol) of 1-N Boc Linifanib, 324 mg of HOBT (2.4 mmol) and 460 mg of EDCl (2.4 mmol) to dissolve in 50 ml of dichloromethane, stirred the reaction for 0.5 h, controlled the reaction temperature at 20~40° C. Slowly added 2195 mg of the intermediate compound 2 (1.92 mmol) prepared in example 12, and finally DIPEA 516 mg (4.0 mmol) was added, the reaction was stirred for 12 h, and the reaction was completed by TLC (DCM/MeOH=40:1). The reaction solution was diluted with 100 ml of dichloromethane, washed twice with 250 ml of deionized water, and the organic phase was separated. The organic phase was washed with 150 ml of saturated sodium solution, separated and dried with anhydrous sodium sulfate. The desiccant was filtered off and the filtrate was concentrated at low temperature to give a brown oily object. The oily object was subjected to silica gel column chromatography (DCM:MeOH=0:1 to 100:1) to yield 724 mg of a white solid powder, the yield rate was 28.3%

Example 14 Preparation of Target Compound 5

Weighed 1008 mg of the intermediate compound 3 (0.63 mmol) prepared in Example 13 and dissolve it in 20 ml of dichloromethane. Controlled the reaction temperature at −55° C. Slowly added 3 ml (0.04 mmol) of trifluoroacetic acid to maintain the reaction temperature. The reaction was stirred for 20-24 h, and the reaction was completed by TLC (DCM/MeOH=40:1). The reaction solution was diluted with 40 ml of dichloromethane, washed twice with 120 ml of deionized water, twice with 60 ml of 5% sodium hydrogen carbonate solution, and twice with 120 ml of deionized water. The organic phase was separated, and the organic phase was dried with anhydrous sodium sulfate. The desiccant was filtered off and the filtrate was concentrated at low temperature to give a red brown oily object. The oily object was subjected to chromatography to give 237 mg of a white solid powder, yield rate was 33.6%. HPLC purity: 97.2% (214 nm), 98.4% (254 nm). MS (ESI): m/z 1120.0 [M+1]$^+$ The chemical structure is:

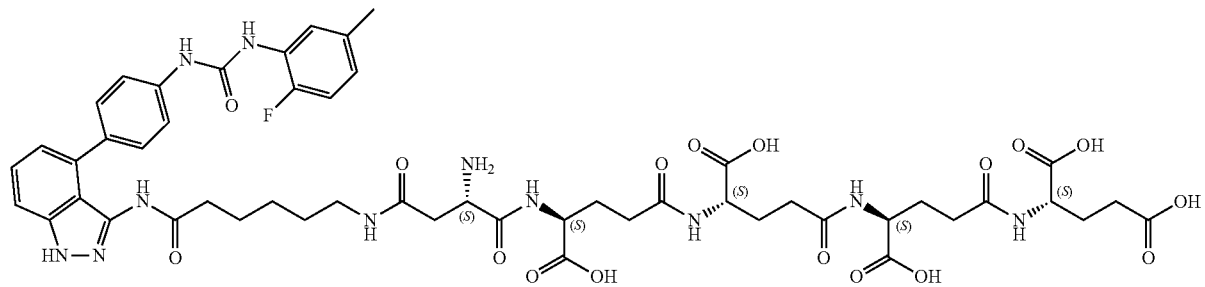

Examples 15-18: Preparation of Target Compound 6

Example 15 Preparation of Intermediate Compound 1

Weighed 304 mg of benzyl-(6-amino)hexaneate hydrochloride (1.18 mmol), 238 mg of HOBT (1.76 mmol), 192 mg of EDCl (1.76 mmol) to dissolve in 50 ml of dichloromethane, stirred at room temperature. Controlled reaction temperature at 20~40° C. Slowly added 2406 mg of Asp(Boc)-Glu(OtBu)-Glu(OtBu)-Glu(OtBu)-Glu(OtBu)-Glu(OtBu)-Glu(OtBu)-Glu(OtBu)-Glu(OtBu)-Glu(OtBu)-(OtBu) (1.23 mmol), maintained the reaction temperature and the reaction was stirred for 4 h, and the reaction was completed by TLC (DCM/MeOH=40:1). The reaction solution was diluted with 100 ml of dichloromethane, washed twice with 250 ml of deionized water, and the organic phase was separated. The organic phase was washed with 150 ml saturated sodium solution and separated. The desiccant was filtered off and the filtrate was concentrated at low temperature to give a brown oily object. The oily object was subjected to silica gel column chromatography (petrol ether/acetone=10:1 to 2:1) to give 724 mg of a yellow solid powder, the yield rate was 28.4%.

Example 16 Preparation of Intermediate Compound 2

907 mg of the intermediate compound 1 (0.42 mmol) prepared in Example 15 was weighed and dissolved in 60 ml of anhydrous methanol, and 10% Pd/C 25 mg was added under nitrogen atmosphere, and hydrogen was introduced and exchanged three times. The reaction was controlled at 2 MPa in the atmosphere, and the reaction was carried out at 20-65° C. for 6-12 h. The reaction was completed by TLC (DCM/MeOH=40:1). The reaction solution was filtered under nitrogen atmosphere to recover palladium carbon. The filtrate was concentrated at low temperature to give a yellow brown oily object. The oily object was subjected to chromatography to give 357 mg of a pale yellow solid powder, the yield rate was 41.1%.

Example 17 Preparation of Intermediate Compound 3

Weighed 760 mg of 1-N Boc Linifanib (1.6 mmol), 324 mg of HOBT (2.4 mmol) and 460 mg of EDCl (2.4 mmol) to dissolve in 250 ml of dichloromethane, stirred the reaction for 0.5 h, controlled the reaction temperature at 20~40° C. Slowly added 3972 mg of the intermediate compound 2 (1.92 mmol) prepared in example 16, and finally DIPEA 516 mg (4.0 mmol) was added, the reaction was stirred for 12 h, and the reaction was completed by TLC (DCM/MeOH=40:1). The reaction solution was diluted with 100 ml of dichloromethane, washed twice with 250 ml of deionized water, and the organic phase was separated. The organic phase was washed with 150 ml of saturated sodium solution, separated, and dried with anhydrous sodium sulfate. The desiccant was filtered off and the filtrate was concentrated at low temperature to give a brown oily object. The oil object was subjected to silica gel column chromatography (DCM:MeOH=0:1 to 100:1) to give 910 mg of a white solid powder; the yield rate was 22.5%.

Example 18 Preparation of Target Compound 6

1592 mg of the intermediate compound 3 (0.63 mmol) prepared in Example 17 was weighed and dissolved in 60 ml of dichloromethane, and the reaction temperature was −5 to 5° C., and 3 ml (0.04 mmol) of trifluoroacetic acid was slowly added to maintain the reaction temperature. The reaction was stirred for 20-24 h, and the reaction was completed by TLC (DCM/MeOH=40:1). The reaction solution was diluted with 40 ml of dichloromethane, washed twice with 120 ml of deionized water, twice with 60 ml of 5% sodium hydrogen carbonate solution, and twice with 120 ml of deionized water. The organic phase was separated and dried with anhydrous sodium sulfate. The desiccant was filtered off and the filtrate was concentrated at low temperature to give a red brown oily object. The oily object was subjected to chromatography to give 255 mg of a white solid powder, the yield rate was 22.9%. HPLC purity: 96.5% (214 nm), 97.7% (254 nm). MS (ESI): m/z 1765.0 [M+1]$^+$ The chemical structure is:

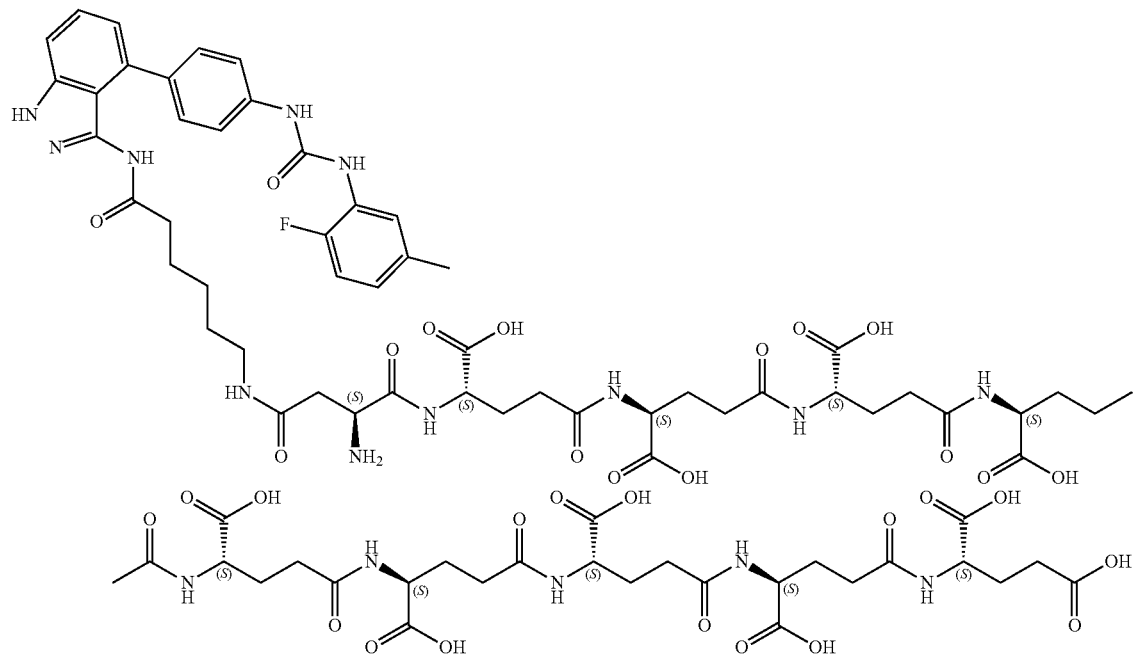

Examples 19-22: Preparation of Target Compound 7

Example 19 Preparation of Intermediate Compound 1

404 mg of Benzyl-(12-amino)dodecanoate hydrochloride (1.18 mmol), 238 mg of HOBT (1.76 mmol), and 192 mg of EDCl (1.76 mmol) were weighed and dissolved in 50 ml of dichloromethane, stirred at room temperature. Controlled reaction temperature at 20~40° C. Slowly added 584 mg of Asp(Boc)-Glu(OtBu)-(OtBu) (1.23 mmol), maintained the reaction temperature, stirred the reaction for 4 h. The reaction was detected to be complete by TLC (DCM/MeOH=40:1). The reaction solution was diluted with 100 ml of dichloromethane, washed twice with 250 ml of deionized water, and the organic phase was separated. The organic phase was washed with 150 ml of saturated sodium solution, separated, and dried with anhydrous sodium sulfate. The desiccant was filtered off and the filtrate was concentrated at low temperature to give a brown oily object. This oily object was subjected to silica gel column chromatography (petroleum ether/acetone=10:1 to 2:1) to yield 320 mg of a yellow solid powder. The yield rate was 35.6%.

Example 20 Preparation of Intermediate Compound 2

2614 mg of the intermediate compound 1 (3.43 mmol) prepared in Example 19 was weighed and dissolved in 100 ml of anhydrous methanol, 10% Pd/C 50 mg was added under nitrogen atmosphere, and hydrogen was introduced and exchanged for 3 times. The reaction was controlled at 2 MPa in the atmosphere, and the reaction was carried out at 20-65° C. for 6-12 h. The reaction was completed by TLC (DCM/MeOH=40:1). The reaction solution was filtered under nitrogen atmosphere to recover palladium carbon. The filtrate was concentrated at low temperature to give a yellow brown oily object. The oily object was subjected to chromatography to give 1293 mg of a pale-yellow solid powder, and yield rate was 56.1%.

Example 21 Preparation of Intermediate Compound 3

Weighed 760 mg of 1-N Boc Linifanib (1.6 mmol), 324 mg of HOBT (2.4 mmol), 460 mg of EDCl (2.4 mmol) in 50 ml of dichloromethane, stirred the reaction for 0.5 h, controlled the reaction temperature at 2040° C. Slowly added 1098 mg of the intermediate compound 2 (1.92 mmol) prepared in example 20, and finally DIPEA 516 mg (4.0 mmol) was added and the reaction was stirred for 12 h, and the reaction was completed by TLC (DCM/MeOH=40:1). The reaction solution was diluted with 100 ml of dichloromethane, washed twice with 250 ml of deionized water, and the organic phase was separated. The organic phase was washed with 150 ml of saturated sodium solution, separated, and dried with anhydrous sodium sulfate. The desiccant was filtered off and the filtrate was concentrated at low temperature to give a brown oily object. The oily object was subjected to silica gel column chromatography (DCM:MeOH=1:1 to 100:1) to give 511 mg of a white powder, and the yield rate was 28.3%.

Example 22 Preparation of Target Compound 7

Weighed 711 mg of the intermediate compound 3 (0.63 mmol) prepared in Example 21 and dissolve it in 20 ml of dichloromethane. Controlled the reaction temperature at −5~5° C. Slowly add 3 ml (0.04 mmol) of trifluoroacetic acid to maintain the reaction temperature. The reaction was stirred for 20-24 h, and the reaction was completed by TLC (DCM/MeOH=40:1). The reaction solution was diluted with 40 ml of dichloromethane, washed twice with 120 ml of deionized water, twice with 60 ml of 5% sodium hydrogen carbonate solution, and twice with 120 ml of deionized water. The organic phase was separated, and the organic phase dried with anhydrous sodium sulfate. The desiccant was filtered off and the filtrate was concentrated at low temperature to give a red brown oily object. The oily object was subjected to chromatography to give 193 mg of a white solid powder, yield rate was 37.4%. HPLC purity: 94.73% (214 nm), 98.57% (254 nm). MS (ESI): m/z 817.1 [M+1]$^+$ The chemical structure is:

Examples 23-26: Preparation of Target Compound 8 (Linifanib-$C_{12}$-$AA_5$)

Example 23 Preparation of Intermediate Compound 1

404 mg of Benzyl-(12-amino)dodecanoate hydrochloride (1.18 mmol), 238 mg of HOBT (1.76 mmol), and 192 mg of EDCl (1.76 mmol) were weighed and dissolved in 250 ml of dichloromethane, stirred at room temperature. Controlled reaction temperature at 20~40° C. Slowly added 1267 mg of Asp(Boc)-Glu(OtBu)-Glu(OtBu)-Glu(OtBu)-Glu(OtBu)-(OtBu) (1.23 mmol), and maintained the reaction temperature. Stir-reacted for 4 h, and the reaction was completed by TLC (DCM/MeOH=40:1). The reaction solution was diluted with 100 ml of dichloromethane, washed twice with 250 ml of deionized water, and the organic phase was separated. The organic phase was washed with 150 ml saturated sodium solution, separated, and dried with anhydrous sodium sulfate. The desiccant was filtered off and the filtrate was concentrated at low temperature to give a brown oily object. The oily object was subjected to silica gel column chromatography (petroleum ether/acetone=10:1 to 2:1) to give 553 mg of a yellow solid powder, the yield rate was 35.6%.

Example 24 Preparation of Intermediate Compound 2

Weighed 4000 mg (3.0 mmol) of the intermediate compound 1 prepared in Example 23, dissolved in 100 ml of anhydrous methanol, 10% Pd/C 50 mg under nitrogen atmosphere, and replaced with hydrogen for 3 times. The reaction was controlled at 2 MPa in the atmosphere, and the reaction was carried out at 20-65° C. for 6-12 h. The reaction was completed by TLC (DCM/MeOH=40:1). The reaction solution was filtered under nitrogen atmosphere to recover palladium carbon. The filtrate was concentrated at low temperature to give a yellow brown oily object. The oily object was subjected to chromatography to give 1595 mg of a pale-yellow solid powder, the yield rate was 42.8%. $^1$HNMR (CDCl3) δ1.27 (brs, 14H), 1.46~1.47 (m, 54H), 1.65~1.85 (m, 8H), 2.34~2.35 (brs, 16H), 3.06~3.36 (brs, 2H), 4.46-4.52 (m, 5H), 6.31 (brs, 1H, —NH—C=O), 6.68 (brs, 1H, —NH—C=O), 6.91 (brs, 2H, —NH—C=O), 7.19 (brs, 1H, —NH—C=O), 7.54 (brs, 1H, —NH—C=O). $^{13}$CNMR (CDCl3) δ 192.97, 190.34, 173.02, 172.22, 172.00, 171.81, 171.22, 171.08, 170.76, 82.42, 82.27, 82.08, 82.02, 80.64, 80.53, 52.35, 51.83, 51.44, 39.84, 33.79, 32.52, 32.15, 31.61, 31.11, 29.26, 29.11, 28.97, 28.92, 28.86, 28.78, 28.71, 28.48, 28.33, 28.10, 28.01, 27.98, 27.76, 27.65, 26.68, 24.61, 12.10.

The chemical structure is:

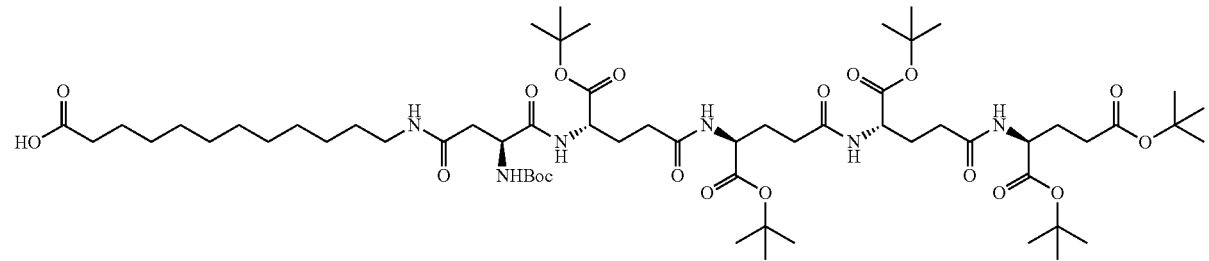 [SMILES: CC(C)(C)OC(=O)CC[C@H](NC(=O)CC[C@H](NC(=O)CC[C@H](NC(=O)CC[C@H](NC(=O)[C@H](CC(=O)NCCCCCCCCCCCC(=O)O)NC(=O)OC(C)(C)C)C(=O)OC(C)(C)C)C(=O)OC(C)(C)C)C(=O)OC(C)(C)C)C(=O)OC(C)(C)C]

Example 25 Preparation of Intermediate Compound 3

Weighed 760 mg of 1-N Boc Linifanib (1.6 mmol), 324 mg of HOBT (2.4 mmol), and 460 mg of EDCl (2.4 mmol) to dissolve in 250 ml of dichloromethane, stirred the reaction for 0.5 h, controlled the reaction temperature at 20~40° C. Slowly added 2340 mg (1.9 mmol) of the intermediate compound 2 prepared in example 24, and finally DIPEA 516 mg (4.0 mmol) was added, the reaction was stirred for 12 h, and the reaction was completed by TLC (DCM/MeOH=40:1). The reaction solution was diluted with 100 ml of dichloromethane, washed twice with 250 ml of deionized water, and the organic phase was separated. The organic phase was washed with 150 ml of saturated sodium solution, separated, and dried with anhydrous sodium sulfate. The desiccant was filtered off and the filtrate was concentrated at low temperature to give a brown oily object. The oily object was subjected to silica gel column chromatography (DCM:MeOH=0:1 to 100:1) to give 882 mg of a white solid powder; the yield rate was 32.7%.

Example 26 Preparation of Target Compound 8 (Linifanib-$C_{12}$-$AA_5$)

Weighed 1062 mg (0.63 mmol) of the intermediate compound 3 prepared in Example 25 and dissolved it in 60 ml of dichloromethane, and slowly added 3 ml (0.04 mmol) of trifluoroacetic acid at a reaction temperature of −5 to 5° C. to maintain the reaction temperature. The reaction was stirred for 20-24 h, and the reaction was completed by TLC (DCM/MeOH=40:1). The reaction solution was diluted with 40 ml of dichloromethane, washed twice with 120 ml of deionized water, twice with 60 ml of 5% sodium hydrogen carbonate solution, and twice with 120 ml of deionized water. The organic phase was separated, and the organic phase dried with anhydrous sodium sulfate. The desiccant was filtered off and the filtrate was concentrated at low temperature to give a red brown oily object. The oily object was subjected to chromatography to give 240 mg of a white solid powder, yield rate was 31.7%. $^1$HNMR (400 MHz, DMSO-d6) δ: 9.51 (s, 1H), 8.97 (s, 1H), 8.56 (s, 1H), 8.32 (d, J=8.4 Hz, 1H), 8.18 (s, 1H), 8.02-7.96 (m, 4H), 7.66-7.57 (m, 3H), 7.42 (d, J=8.8 Hz, 2H), 7.19-7.08 (m, 2H), 6.82-6.81 (m, 1H), 5.18 (s, 2H), 4.16-3.98 (m, 6H), 3.07-2.96 (m, 4H), 2.67-2.63 (m, 2H), 2.28 (s, 3H), 2.24-2.14 (m, 8H), 2.03-1.87 (m, 5H), 1.77-1.67 (m, 4H), 1.37-1.23 (m, 18H). HPLC purity: 99.3% (214 nm), 99.1% (254 nm). MS (ESI): m/z 1204.5 [M+1]$^+$ The chemical structure is:

(OtBu)-Glu(OtBu)-Glu(OtBu)-Glu(OtBu)-Glu (OtBu)-Glu(OtBu)-(OtBu), maintained the reaction temperature and stir-reacted for 4 h, and the reaction was completed by TLC (DCM/MeOH=40:1). The reaction solution was diluted with 100 ml of dichloromethane, washed twice with 250 ml of deionized water, and the organic phase was separated. The organic phase was washed with 150 ml saturated sodium solution, separated, and dried with anhydrous sodium sulfate. The desiccant was filtered off and the filtrate was concentrated at low temperature to give a brown oily object. This oily object was subjected to silica gel column chromatography (petroleum ether/acetone=10:1 to 2:1) to yield 627 mg of a yellow solid powder, yield rate was 23.7%.

Example 28 Preparation of Intermediate Compound 2

6732 mg (3.0 mmol) of the intermediate compound 1 prepared in Example 27 was weighed and dissolved in 200 ml of anhydrous methanol, 10% Pd/C 50 mg was added under nitrogen atmosphere, and hydrogen was introduced and exchanged for 3 times. The reaction was controlled at 2 MPa in the atmosphere, and the reaction was carried out at 20-65° C. for 6-12 h. The reaction was completed by TLC (DCM/MeOH=40:1). The reaction solution was filtered under nitrogen atmosphere to recover palladium carbon. The filtrate was concentrated at low temperature to give a yellow brown oily object. The oily object was subjected to chromatography to give 2480 mg of a pale-yellow solid powder, yield rate was 38.4%.

Example 29 Preparation of Intermediate Compound 3

Weighed 760 mg (1.6 mmol) of 1-N Boc Linifanib, 324 mg (2.4 mmol) of HOBT and 460 mg (2.4 mmol) of EDCl, and dissolved in 250 ml of dichloromethane, stirred the reaction for 0.5 h, controlled the reaction temperature at 2040° C. Slowly added 4134 mg (1.92 mmol) of intermediate compound 2 prepared in example 28 and finally

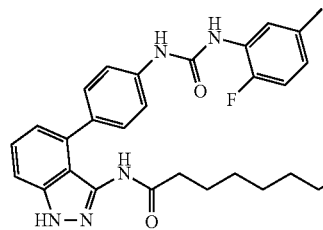

Linifanib-$C_{12}$-$AA_5$

Examples 27-30: Preparation of Target Compound 9

Example 27 Preparation of Intermediate Compound 1

404 mg (1.18 mmol) of Benzyl-(12-amino)dodecanoate hydrochloride, 238 mg (1.76 mmol) of HOBT, and 192 mg (1.76 mmol) of EDCl were weight and dissolved in 250 ml of dichloromethane, stirred at room temperature. Controlled reaction temperature at 2040° C. Slowly added 2406 mg (1.23 mmol) of Asp(Boc)-Glu(OtBu)-Glu(OtBu)-Glu DIPEA 516 mg (4.0 mmol) was added, the reaction was stirred for 12 h, and the reaction was completed by TLC (DCM/MeOH=40:1). The reaction solution was diluted with 100 ml of dichloromethane, washed twice with 250 ml of deionized water, and the organic phase was separated. The organic phase was washed with 150 ml of saturated sodium solution, separated, and dried with anhydrous sodium sulfate. The desiccant was filtered off and the filtrate was concentrated at low temperature to give a brown oily object. The oily object was subjected to silica gel column chromatography (DCM:MeOH=1:1 to 100:1) to give 777 mg of a white solid powder, and the yield rate was 18.6%.

Example 30 Preparation of Target Compound 9

Weighed 1645 mg (0.63 mmol) of the intermediate compound 3 prepared in Example 29, dissolved in 60 ml of dichloromethane, and slowly added 3 ml (0.04 mmol) of trifluoroacetic acid at a reaction temperature of −5 to 5° C. to maintain the reaction temperature. The reaction was stirred for 20-24 h, and the reaction was completed by TLC (DCM/MeOH=40:1). The reaction solution was diluted with 40 ml of dichloromethane, washed twice with 120 ml of deionized water, twice with 60 ml of 5% sodium hydrogen carbonate solution, and twice with 120 ml of deionized water. The organic phase was separated, and the organic phase dried with anhydrous sodium sulfate. The desiccant was filtered off and the filtrate was concentrated at low temperature to give a red brown oily object. The oily object was subjected to chromatography to give 379 mg of a white solid powder, yield rate was 32.5%. HPLC purity: 94.6% (214 nm), 96.9% (254 nm). MS (ESI): m/z 1849.7 [M+1]$^+$ Chemical structure is:

of dichloromethane, and the reaction temperature was −5 to 5° C., and 3 ml (0.04 mmol) of trifluoroacetic acid was slowly added to maintain the reaction temperature. The reaction was stirred for 1.5 to 2 h, and the reaction was completed by TLC (DCM/MeOH=40:1). The reaction solution was diluted with 50 ml of dichloromethane, washed twice with 120 ml of deionized water, twice with 60 ml of 5% sodium hydrogen carbonate solution, and twice with 120 ml of deionized water. The organic phase was separated and dried with anhydrous sodium sulfate. The desiccant was filtered off and the filtrate was concentrated to a yellow oily object. The oily object was chromatographed to give 118 mg of a yellow oily object, the yield rate was 70.4%.

Example 33 Preparation of Target Compound 10

336 mg (0.58 mmol) of the intermediate Md prepared in Example 32 was weighed and dissolved in 30 ml of anhydrous methanol, and 10% Pd/C 25 mg was added under nitrogen atmosphere, and hydrogen was introduced and

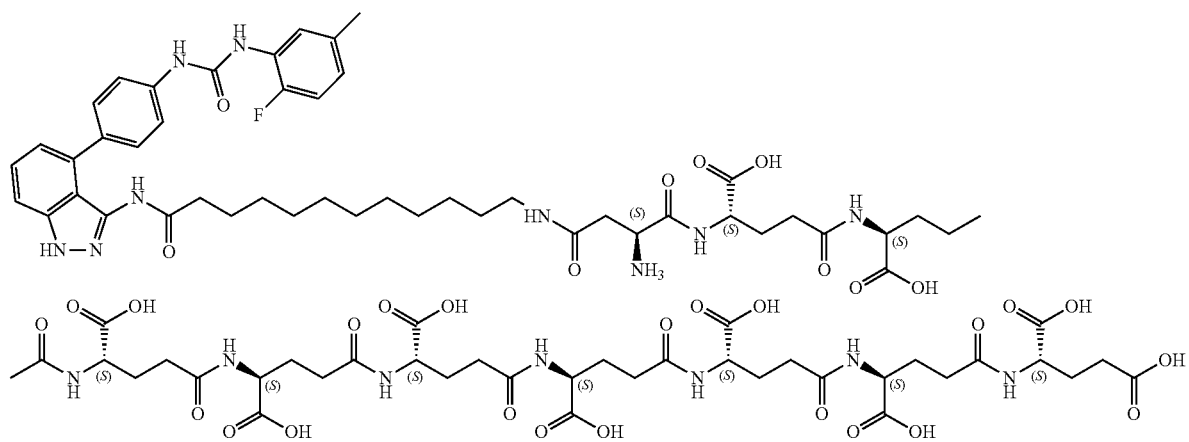

Experiments 31-33: Preparation of Target Compound 10

Example 31 Preparation of Metabolite Intermediate Compound Mc

Weighed 137 mg (0.42 mmol) of Boc-L-aspartic acid 1-benzyl ester, 77.8 mg (0.58 mmol) of HOBT, and 110 mg (0.58 mmol) of EDCl and dissolved in 10 ml of dichloromethane, stirred the reaction for 0.5 h, controlled a reaction temperature of 20 to 40° C. 181 mg (0.38 mmol) of 1-N Boc Linifanib was slowly added and finally DIPEA 124 mg (0.96 mmol) was added. After the addition, the reaction temperature was maintained for 4 h, and the reaction was completed by TLC (DCM/MeOH=40:1). The reaction mixture was diluted with 50 ml of methylene chloride and washed twice with 100 ml of deionized water. The desiccant was filtered off and the filtrate was concentrated at low temperature to give a brown oily object. The oily object was subjected to silica gel column chromatography (DCM:MeOH=1:1 to 30:1) to give 162 mg of a yellow oily object, the yield rate was 54.7%.

Example 32 Preparation of Metabolite Intermediate Compound Md 226 mg (0.29 mmol) of the intermediate compound Mc prepared in Example 31 was weighed and dissolved in 20 ml exchanged for 3 times. The reaction was controlled at 2 MPa in the atmosphere, the reaction was carried out at 2065° C. for 612 h, and the reaction was completed by TLC (DCM/MeOH=40:1). The reaction solution was filtered under nitrogen atmosphere to recover palladium carbon. The filtrate was concentrated at low temperature to give a pale-yellow oily object. The oily object was subjected to chromatography to give 153 mg of a white solid powder, yield rate was 53.7%. HPLC purity: 94.6% (214 nm), 97.3% (254 nm). MS (ESI): m/z 491.0[M+1]$^+$ The chemical structure is:

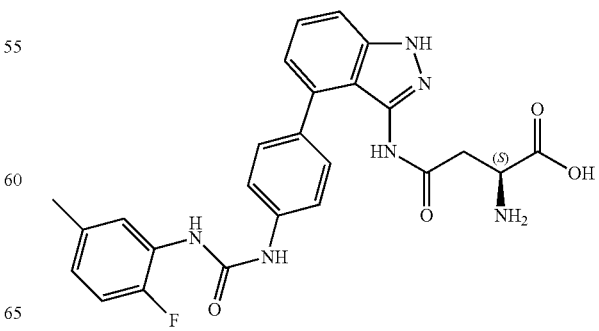

Examples 34-38: Preparation of Target Compound 11

Example 34 Preparation of Metabolite Intermediate Compound Ma 136 mg (0.59 mmol) of 6-(BOC-amino)hexane acid, 107 mg (0.8 mmol) of HOBT, and 152 mg (0.8 mmol) of EDCl were weighed and dissolved in 10 ml of dichloromethane, stirred the reaction for 0.5 h, controlled the reaction temperature at 2040° C. 252 mg (0.53 mmol) of 1-N Boc Linifanib was slowly added and finally DIPEA 171 mg (1.3 mmol) was added. After the addition, the reaction temperature was maintained and stir-reacted for 4 h, and the reaction was completed by TLC (DCM/MeOH=40:1). The reaction mixture was diluted with 50 ml of methylene chloride and washed twice with 100 ml of deionized water, and the organic phase was separated and dried with anhydrous sodium sulfate. The desiccant was filtered off and the filtrate was concentrated at low temperature to give a brown oily object. The oily object was subjected to silica gel column chromatography (DCM:MeOH=1:1 to 30:1) to give 167 mg of a yellow oily object, and the yield rate was 45.8%.

Example 35 Preparation of Metabolite Intermediate Compound Mb 227 mg (0.33 mmol) of the intermediate Ma prepared in Example 34 was weighed and dissolved in 20 ml of dichloromethane, and the reaction temperature was a −5 to 5° C., and 3 ml (0.04 mmol) of trifluoroacetic acid was slowly added; the reaction temperature was maintained and stir-reacted for 1.52 h, and the reaction was completed by TLC (DCM/MeOH=40:1). The reaction solution was diluted with 50 ml of dichloromethane, washed twice with 120 ml of deionized water, twice with 60 ml of 5% sodium hydrogen carbonate solution, and twice with 120 ml of deionized water. The organic phase was separated and dried with anhydrous sodium sulfate. The desiccant was filtered off and the filtrate was concentrated at low temperature to give a red brown oily object. The oily object was subjected to chromatography to give 143 mg of a yellow oily object, the yield rate was 88.6%.

Example 36 Preparation of Metabolite Intermediate Compound Mc 137 mg (0.42 mmol) of Boc-L-aspartic acid 1-benzyl ester, 77.8 mg (0.58 mmol) of HOBT and 110 mg (0.58 mmol) EDCl were weighed and dissolved in 10 ml of dichloromethane, stirred the reaction for 0.5 h, controlled the reaction temperature at 20 to 40° C. 185 mg (0.38 mmol) of the intermediate Mb prepared in Example 35 was slowly added, and finally DIPEA 124 mg (0.96 mmol) was added. After the addition, the reaction temperature was maintained and stir-reacted for 4 h, the reaction was completed by TLC (DCM/MeOH=40:1). The reaction mixture was diluted with 50 ml of methylene chloride and washed twice with 100 ml of deionized water. The desiccant was filtered off and the filtrate was concentrated at low temperature to give a brown oily object. The oily object was subjected to silica gel column chromatography (DCM:MeOH=1:1 to 30:1) to give 106 mg of a yellow oily object, the yield rate was 35.2%.

Example 37 Preparation of Metabolite Intermediate Compound Md 230 mg (0.29 mmol) of the intermediate compound Mc prepared in Example 36 was weighed and dissolved in 20 ml of dichloromethane, and the reaction temperature was controlled at −5 to 5° C. Slowly add 3 ml (0.04 mmol) of trifluoroacetic acid to maintain the reaction temperature. The reaction was stirred for 1.5 to 2 h, and the reaction was completed by TLC (DCM/MeOH=40:1). The reaction solution was diluted with 50 ml of dichloromethane, washed twice with 120 ml of deionized water, twice with 60 ml of 5% sodium hydrogen carbonate solution, and twice with 120 ml of deionized water. The organic phase was separated and dried with anhydrous sodium sulfate. The desiccant was filtered off and the filtrate was concentrated to a yellow oily object. The oily object was subjected to chromatography to give 131 mg of a yellow oily object, the yield rate was 65.4%.

Example 38 Preparation of Target Compound 11

425 mg (0.61 mmol) of the intermediate Md prepared in Example 37 was weighed and dissolved in 30 ml of anhydrous methanol, and 10% Pd/C 25 mg was added under nitrogen atmosphere, and hydrogen was introduced and exchanged for 3 times. The reaction was controlled at 2 MPa in the atmosphere, the reaction was carried out at 20~65° C. for 6~12 h, and the reaction was completed by TLC (DCM/MeOH=40:1). The reaction solution was filtered under nitrogen atmosphere to recover palladium carbon. The filtrate was concentrated at low temperature to give a pale-yellow oily object. The oily object was subjected to p chromatography to give 198 mg of a white solid powder, and the yield rate was 53.7%. HPLC purity: 95.8% (214 nm), 99.5% (254 nm). MS (ESI): m/z 604.3[M+1]$^+$ The chemical structure is:

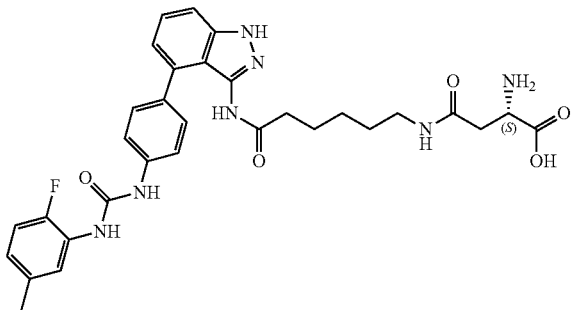

Examples 39-43: Preparation of Target Compound 12 (Linifanib-$C_{12}$-Asp)

Example 39 Preparation of Metabolite Intermediate Compound Ma 186 mg (0.59 mmol) of 12-(BOC-amino)dodecanoic acid, 107 mg (0.8 mmol) of HOBT and 152 mg (0.8 mmol) of EDCl were weighed and dissolved in 10 ml of dichloromethane, stirred the reaction for 0.5 h, controlled the reaction temperature at 20~40° C. Slowly added 252 mg (0.53 mmol) of 1-N Boc Linifanib and finally added DIPEA 171 mg (1.3 mmol). The reaction temperature was maintained and stir-reacted for 4 hr. The reaction was completed by TLC (DCM/MeOH=40:1). The reaction mixture was diluted with 50 ml of methylene chloride and washed twice with 100 ml of deionized water. The desiccant was filtered off and the filtrate was concentrated at low temperature to give a brown oily object. The oily object was subjected to silica gel column chromatography (DCM:MeOH=1:1 to 30:1) to give 173 mg of a yellow oily object, and the yield rate was 42.2%.

Example 40 Preparation of Metabolite Intermediate Compound Mb 255 mg (0.33 mmol) of the intermediate Ma prepared in Example 39 was weighed and dissolved in 20 ml of dichloromethane, and the reaction temperature was −5 to 5° C. 3 ml (0.04 mmol) of trifluoroacetic acid was slowly added to maintain the reaction temperature. Stir-reacted for 1.5~2 h, and the reaction was completed by TLC (DCM/MeOH=40:1). The reaction solution was diluted with 50 ml of dichloromethane, washed twice with 120 ml of deionized water, twice with 60 ml of 5% sodium hydrogen carbonate solution, and twice with 120 ml of deionized water. The organic phase was separated and dried with anhydrous sodium sulfate. The desiccant was filtered off and the filtrate was concentrated at low temperature to give a red brown oily object. The oily object was chromatographed to give 155 mg of a yellow oily object, the yield rate was 82%.

Example 41 Preparation of Metabolite Intermediate Compound Mc 137 mg (0.42 mmol) of Boc-L-aspartic acid 1-benzyl ester, 77.8 mg (0.58 mmol) of HOBT, and 110 mg (0.58 mmol) of EDCl were weighed and dissolved in 10 ml of dichloromethane, stirred the reaction for 0.5 h, controlled the reaction temperature of 20 to 40° C. 220 mg (0.38 mmol) of the intermediate Mb prepared in Example 40 was slowly added at finally DIPEA 124 mg (0.96 mmol) was added. The reaction was stirred for 4 h and completed by TLC (DCM/MeOH=40:1). The reaction mixture was diluted with 50 ml of methylene chloride and washed twice with 100 ml of deionized water. The desiccant was filtered off and the filtrate was concentrated at low temperature to give a brown oily object. The oily object was subjected to silica gel column chromatography (DCM:MeOH=1:0-30:1) to give 183 mg of a yellow oily object, the yield rate was 54.9%.

Example 42 Preparation of Metabolite Intermediate Compound Md 250 mg (0.29 mmol) of the intermediate compound Mc prepared in Example 41 was weighed and dissolved in 20 ml of dichloromethane, and slowly added 3 ml (0.04 mmol) of trifluoroacetic acid at a reaction temperature of −5 to 5° C. to maintain the reaction temperature. The reaction was stirred for 1.5 to 2 h, and the reaction was completed by TLC (DCM/MeOH=40:1). The reaction solution was diluted with 50 ml of dichloromethane, washed twice with 120 ml of deionized water, twice with 60 ml of 5% sodium hydrogen carbonate solution, and twice with 120 ml of deionized water. The organic phase was separated and dried with anhydrous sodium sulfate. The desiccant was filtered off and the filtrate was concentrated to a yellow oily object. The oily object was subjected to chromatography to give 153 mg of a yellow oily object, the yield rate was 67.6%.

Example 43 Preparation of Target Compound 12 (Linifanib-$C_{12}$-Asp)

210 mg (0.27 mmol) of the intermediate Md prepared in Example 42 was weighed and dissolved in 30 ml of anhydrous methanol, added 10% Pd/C 25 mg under nitrogen protection, hydrogen was introduced and exchanged for three times, and the reaction was controlled at 2 MPa in the atmosphere. The reaction was carried out at 20~65° C. for 6~12 h, and the reaction was completed by TLC (DCM/MeOH=40:1). The reaction solution was filtered under nitrogen atmosphere to recover palladium carbon. The filtrate was concentrated at low temperature to give a pale-yellow oily object. The oily object was subjected to chromatography to give 91 mg of a white solid powder, and the yield rate was 49.2%. $^1$HNMR (DMSO) δ: 1.109-1.127 (m, 16H), 1.234-1.352 (m, 2H), 1.902-1.920 (m, 2H), 2.278 (s, 3H), 2.642-2.741 (m, 2H), 2.993-3.040 (m, 2H), 3.740-3.806 (m, 1H), 6.796-6.808 (m, 1H), 6.971-6.988 (m, 1H), 7.089-7.118 (m, 1H), 7.320-7.407 (m, 3H), 7.453-7.505 (m, 3H), 8.022-8.042 (d, J=8 Hz, 1H), 8.121-8.148 (t, J=5.6 Hz, 1H), 8.524 (s, 1H), 9.219 (s, 1H), 9.424 (s, 1H), 12.956 (s, 1H). HPLC purity: 96.6% (214 nm), 99.9% (254 nm). MS (ESI): m/z 688.4[M+1]$^+$ The chemical structure is:

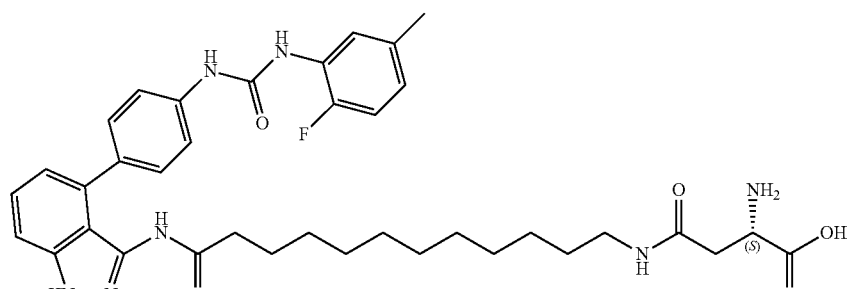

Linifanib-$C_{12}$-Asp

Example 44 Effect of Linifanib Related Compounds on the Proliferation of Tumor Cell Lines This application measured the half-inhibitory concentration (IC50 value) of 13 compounds (Compound 1-12 and Linifanib on 54 commercial tumor cell lines (including 26 liver cancer cell lines) by cell proliferation assay (Alamar Blue assay platform). The difference between compounds 1-12 and the active drug Linifanib activity was compared.

1. Instruments and Materials

Thermo 311 $CO_2$ incubator; Haier biosafety cabinet; Molecular Devices microplate reader; Xiangyi brand L530 desktop low speed centrifuge; Olympus IX51 inverted fluorescence microscope, DMEM, RPMI 1640, MEM, DMEM/F12 1:1 medium, Fetal bovine serum, 0.25% trypsin solution, phosphate buffer (Thermo Fisher Shanghai Co., Ltd.); sigma dimethyl sulfoxide (DMSO), resazurin; 54 commercial tumor cell lines (including 26 liver cancer cell lines). Experimental drugs: compounds 1-12 and active drug Linifanib; chemotherapeutic drug Doxorubicin (HY-15142; Shanghai Qianyuan Biomedical Technology Co., Ltd.).

2. Experimental Methods 2.1 Cultivation of Different Cell Lines 54 cell lines were cultured in a culture medium containing fetal bovine serum and placed in a 5% $CO_2$ incubator at 37° C. for incubation. The cells were all grown in an adherent state, and the growth was observed under an inverted microscope, and subculture was performed when the cell confluence rate reached 80%-90%. The proportion and quantity of passage were determined by experimental needs. The ratio of subculture of this cell line was generally 1:2~1:3.

2.2 Inhibition Effect on the Proliferation of Different Tumor Cell Lines

Cell test: 54 cell lines in logarithmic growth phase were inoculated in 96-well culture plates at 500~1×104/well (the optimal seeding density of each cell line was determined in pre-experiment), After incubating at 37° C. for 4 h in a 5% $CO_2$ humidification incubator, added 10 μL of compounds 1-12 or Linifanib to each well, and tested 9 drug concentration gradients for each compound (diluted from the highest concentration of the test by 3.16 times). The solubility of each compound was different at a starting concentration of 100 or 30 μM, respectively. The QC reference compound Doxorubicin was added simultaneously to each cell line test, and the final drug concentrations were 10, 3.16, 1, 0.31, 0.1, 0.03, 0.01, 0.003, and 0.001 μM, respectively. In addition, a positive control group (100% inhibition) and a negative control group (0% inhibition) were set at the same time. The drug group was repeated for 2 wells per concentration, and the positive control group and the negative control group were repeated for 6 wells. After the culture was continued for 6 days in the incubator, AlamarBlue test operation was followed;

AlamarBlue test procedure: Incubated with 10 μL of AlamarBlue reagent per well for 1-4 h, shook for 1-2 min, MD microplate reader EX: 560 nm, EM: 590 nm wavelength to measure fluorescence, recorded the results, calculated the cell inhibition rate of the compound of the invention. Cell inhibition rate (%)= (A0% inhibition−A administration)/(A0% inhibition−A100% inhibition)×100%, and then using the method of nonlinear regression using GraphPad Prism 5.0 or MATLAB software (usually using four parameters) to graph and obtain a drug dose response curve to obtain an IC50 value of the compound of the present invention acting on a cancer cell line.

3. Results and Analysis 3.1 the IC50 Summary Results of 13 Test Samples (Compounds 1-12 and Linifanib) on 54 Commercial Tumor Cell Lines were Shown in Table 1 and Table 2.

TABLE 1

Summary of IC50 (μM) values of Compounds 1-6 and Linifanib for 54 commercial tumor cell lines

| Tumor cell line number | Tumor cell line name | Compound 1 | Compound 2 | Compound 3 | Compound 4 | Compound 5 | Compound 6 | Linifanib |
|---|---|---|---|---|---|---|---|---|
| 1 | 22RV1 | 8.16 | 11.48 | 19.74 | >100 | >100 | >100 | 7.50 |
| 2 | AN3CA | 0.34 | 0.73 | 1.26 | 24.93 | 41.37 | 55.51 | 0.19 |
| 3 | CCRF-CEM | 6.14 | 10.38 | 14.72 | >100 | >100 | >100 | 5.03 |
| 4 | DLD1 | 18.47 | 29.16 | 41.09 | >100 | >100 | >100 | 11.59 |
| 5 | DU145 | 4.25 | 9.34 | 20.68 | >100 | >100 | >100 | 5.01 |
| 6 | HCCLM3 | 8.24 | 11.97 | 20.88 | >100 | >100 | >100 | 6.67 |
| 7 | HT1080 | 10.37 | 24.89 | 27.52 | >100 | >100 | >100 | 6.40 |
| 8 | HT55 | 24.68 | 40.05 | 53.33 | >100 | >100 | >100 | 22.29 |
| 9 | HuTu80 | 1.98 | 4.26 | 7.64 | 75.38 | >100 | >100 | 1.85 |
| 10 | K562 | 17.25 | 29.46 | 42.19 | >100 | >100 | >100 | 10.85 |
| 11 | KASUMI-1 | 0.02 | 0.05 | 0.12 | 1.53 | 4.26 | 9.88 | 0.01 |
| 12 | KM12 | 3.71 | 5.48 | 7.26 | >100 | >100 | >100 | 1.39 |
| 13 | LC-2-ad | 3.52 | 6.37 | 11.29 | >100 | >100 | >100 | 4.78 |
| 14 | LNCAP-clone-FGC | 15.62 | 26.49 | 40.66 | >100 | >100 | >100 | 11.30 |
| 15 | MDA-MB-231 | 7.61 | 12.38 | 19.82 | >100 | >100 | >100 | 4.03 |
| 16 | MDA-MB-435S | 10.53 | 18.62 | 41.75 | >100 | >100 | >100 | 10.71 |
| 17 | MFM-223 | 3.59 | 6.93 | 8.46 | >100 | >100 | >100 | 1.72 |
| 18 | MG63 | 2.34 | 5.49 | 8.94 | >100 | >100 | >100 | 1.78 |
| 19 | NCI-H1648 | 10.14 | 21.53 | 33.64 | >100 | >100 | >100 | 7.17 |
| 20 | NCI-H1703 | 0.03 | 0.07 | 0.10 | 1.24 | 2.81 | 4.16 | 0.02 |
| 21 | NCI-H2170 | 5.32 | 7.69 | 10.48 | >100 | >100 | >100 | 4.00 |
| 22 | NCI-H526 | 7.45 | 11.26 | 28.49 | >100 | >100 | >100 | 7.80 |
| 23 | NCI-H661 | 20.21 | 36.81 | 55.64 | >100 | >100 | >100 | 13.34 |
| 24 | NCI-H716 | 5.49 | 10.79 | 26.85 | 82.72 | >100 | >100 | 4.10 |
| 25 | SW620 | 3.96 | 6.81 | 11.12 | >100 | >100 | >100 | 2.78 |
| 26 | T.T | 9.24 | 16.87 | 22.96 | >100 | >100 | >100 | 4.86 |
| 27 | TE-15 | 2.94 | 7.29 | 14.62 | >100 | >100 | >100 | 3.60 |
| 28 | TE-6 | 10.46 | 27.62 | 33.38 | >100 | >100 | >100 | 4.09 |
| 29 | Li-7 | 7.29 | 19.47 | 21.63 | >100 | >100 | >100 | 5.43 |
| 30 | JHH1 | 21.39 | 33.86 | 51.39 | >100 | >100 | >100 | 12.16 |
| 31 | JHH2 | 43.57 | 88.25 | >100 | >100 | >100 | >100 | 29.54 |
| 32 | JHH4 | 25.03 | 36.84 | 49.71 | >100 | >100 | >100 | 10.61 |
| 33 | JHH5 | 16.56 | 24.65 | 40.27 | >100 | >100 | >100 | 10.04 |
| 34 | JHH6 | 6.57 | 10.86 | 23.17 | >100 | >100 | >100 | 4.11 |

TABLE 1-continued

Summary of IC50 (μM) values of Compounds 1-6 and Linifanib for 54 commercial tumor cell lines

| Tumor cell line number | Tumor cell line name | Compound 1 | Compound 2 | Compound 3 | Compound 4 | Compound 5 | Compound 6 | Linifanib |
|---|---|---|---|---|---|---|---|---|
| 35 | JHH7 | 1.54 | 4.26 | 7.62 | >100 | >100 | >100 | 1.83 |
| 36 | HUH1 | 4.67 | 7.26 | 12.69 | >100 | >100 | >100 | 3.25 |
| 37 | HUH6 | 52.94 | 79.03 | 94.15 | >100 | >100 | >100 | >30 |
| 38 | HUH7 | 2.89 | 6.33 | 8.14 | >100 | >100 | >100 | 1.67 |
| 39 | Hep3B2.1-7 | 3.29 | 6.32 | 10.41 | >100 | >100 | >100 | 1.96 |
| 40 | HEPG2 | 1.35 | 3.86 | 7.49 | 54.33 | 72.16 | >100 | 0.83 |
| 41 | HLE | 2.84 | 6.47 | 10.84 | >100 | >100 | >100 | 3.93 |
| 42 | HLF | 5.24 | 10.83 | 17.45 | >100 | >100 | >100 | 3.65 |
| 43 | Alexander cells | 4.01 | 7.11 | 9.36 | >100 | >100 | >100 | 4.09 |
| 44 | SK-HEP-1 | 16.57 | 30.96 | 41.29 | >100 | >100 | >100 | 7.11 |
| 45 | SNU182 | 30.91 | 46.25 | 58.17 | >100 | >100 | >100 | 15.16 |
| 46 | SNU354 | 3.59 | 8.62 | 15.26 | >100 | >100 | >100 | 4.58 |
| 47 | SNU387 | 22.26 | 47.91 | 64.38 | >100 | >100 | >100 | 12.32 |
| 48 | SNU398 | 1.75 | 4.63 | 9.57 | >100 | >100 | >100 | 1.91 |
| 49 | SNU423 | 25.41 | 33.19 | 46.78 | >100 | >100 | >100 | 9.24 |
| 50 | SNU449 | 16.47 | 25.69 | 43.92 | >100 | >100 | >100 | 10.19 |
| 51 | SNU475 | 4.81 | 11.16 | 24.95 | >100 | >100 | >100 | 5.37 |
| 52 | SNU739 | 7.63 | 11.28 | 23.64 | >100 | >100 | >100 | 5.45 |
| 53 | SNU761 | 12.60 | 19.46 | 33.81 | >100 | >100 | >100 | 8.98 |
| 54 | SNU886 | 7.24 | 16.93 | 25.38 | >100 | >100 | >100 | 4.48 |

Note:
The cell lines 29-54 in the table indicate the response of the liver cancer cell line to each compound.

TABLE 2

Summary of IC50 (μM) values of compounds 7-12 against 54 commercial tumor cell lines

| Tumor cell line number | Tumor cell line name | Compound 7 | Compound 8 | Compound 9 | Compound 10 | Compound 11 | Compound 12 | Linifanib |
|---|---|---|---|---|---|---|---|---|
| 1 | 22RV1 | >100 | >100 | >100 | 6.37 | >100 | 95.60 | 7.50 |
| 2 | AN3CA | 3.84 | 5.68 | 10.29 | 0.27 | 17.42 | 3.84 | 0.19 |
| 3 | CCRF-CEM | >100 | >100 | >100 | 5.46 | >100 | >100 | 5.03 |
| 4 | DLD1 | >100 | >100 | >100 | 10.48 | >100 | >100 | 11.59 |
| 5 | DU145 | >100 | >100 | >100 | 3.62 | >100 | 83.05 | 5.01 |
| 6 | HCCLM3 | >100 | >100 | >100 | 7.76 | >100 | >100 | 6.67 |
| 7 | HT1080 | >100 | >100 | >100 | 7.83 | >100 | >100 | 6.40 |
| 8 | HT55 | >100 | >100 | >100 | 18.46 | >100 | >100 | 22.29 |
| 9 | HuTu80 | 27.66 | 50.63 | 90.37 | 1.84 | 63.09 | 44.39 | 1.85 |
| 10 | K562 | >100 | >100 | >100 | 14.62 | >100 | >100 | 10.85 |
| 11 | KASUMI-1 | 0.23 | 0.39 | 0.87 | 0.01 | 1.09 | 0.49 | 0.01 |
| 12 | KM12 | 79.14 | >100 | >100 | 2.43 | >100 | 82.46 | 1.39 |
| 13 | LC-2-ad | 46.43 | 82.40 | >100 | 3.33 | >100 | 22.94 | 4.78 |
| 14 | LNCAP-clone-FGC | 95.46 | >100 | >100 | 14.75 | >100 | 70.49 | 11.30 |
| 15 | MDA-MB-231 | >100 | >100 | >100 | 4.63 | >100 | 79.48 | 4.03 |
| 16 | MDA-MB-435S | >100 | >100 | >100 | 9.46 | >100 | >100 | 10.71 |
| 17 | MFM-223 | 88.27 | >100 | >100 | 2.64 | >100 | 53.38 | 1.72 |
| 18 | MG63 | >100 | >100 | >100 | 1.95 | >100 | >100 | 1.78 |
| 19 | NCI-H1648 | >100 | >100 | >100 | 7.42 | >100 | >100 | 7.17 |
| 20 | NCI-H1703 | 0.11 | 0.19 | 0.35 | 0.02 | 0.83 | 0.25 | 0.02 |
| 21 | NCI-H2170 | 48.02 | 75.33 | >100 | 4.28 | >100 | 59.24 | 4.00 |
| 22 | NCI-H526 | >100 | >100 | >100 | 6.93 | >100 | >100 | 7.80 |
| 23 | NCI-H661 | >100 | >100 | >100 | 18.02 | >100 | >100 | 13.34 |
| 24 | NCI-H716 | 41.59 | 44.87 | 77.16 | 5.09 | 67.37 | 35.52 | 4.10 |
| 25 | SW620 | 56.27 | 65.29 | >100 | 3.46 | >100 | 55.56 | 2.78 |
| 26 | T.T | >100 | >100 | >100 | 7.38 | >100 | >100 | 4.86 |
| 27 | TE-15 | >100 | >100 | >100 | 2.58 | >100 | >100 | 3.60 |
| 28 | TE-6 | >100 | >100 | >100 | 6.98 | >100 | >100 | 4.09 |
| 29 | Li-7 | >100 | >100 | >100 | 5.28 | >100 | 90.37 | 5.43 |
| 30 | JHH1 | >100 | >100 | >100 | 14.51 | >100 | >100 | 12.16 |
| 31 | JHH2 | >100 | >100 | >100 | 36.78 | >100 | >100 | 29.54 |
| 32 | JHH4 | >100 | >100 | >100 | 14.37 | >100 | >100 | 10.61 |
| 33 | JHH5 | >100 | >100 | >100 | 13.36 | >100 | >100 | 10.04 |
| 34 | JHH6 | >100 | >100 | >100 | 5.38 | >100 | 85.76 | 4.11 |
| 35 | JHH7 | 63.41 | 94.90 | >100 | 1.36 | >100 | 67.18 | 1.83 |
| 36 | HUH1 | >100 | >100 | >100 | 3.88 | >100 | >100 | 3.25 |
| 37 | HUH6 | >100 | >100 | >100 | 43.76 | >100 | >100 | >30 |
| 38 | HUH7 | 42.18 | 65.38 | 88.49 | 2.24 | >100 | 40.58 | 1.67 |
| 39 | Hep3B2.1-7 | 40.38 | 80.17 | >100 | 2.43 | >100 | 79.63 | 1.96 |

TABLE 2-continued

Summary of IC50 (μM) values of compounds 7-12 against 54 commercial tumor cell lines

| Tumor cell line number | Tumor cell line name | Compound 7 | Compound 8 | Compound 9 | Compound 10 | Compound 11 | Compound 12 | Linifanib |
|---|---|---|---|---|---|---|---|---|
| 40 | HEPG2 | 9.53 | 11.50 | 33.62 | 0.97 | 30.06 | 9.27 | 0.83 |
| 41 | HLE | 88.26 | >100 | >100 | 2.16 | >100 | >100 | 3.93 |
| 42 | HLF | 72.64 | >100 | >100 | 4.85 | 95.66 | >100 | 3.65 |
| 43 | Alexander cells | >100 | >100 | >100 | 3.79 | >100 | 77.09 | 4.09 |
| 44 | SK-HEP-1 | >100 | >100 | >100 | 14.93 | >100 | >100 | 7.11 |
| 45 | SNU182 | >100 | >100 | >100 | 22.13 | >100 | >100 | 15.16 |
| 46 | SNU354 | >100 | >100 | >100 | 3.33 | >100 | 97.28 | 4.58 |
| 47 | SNU387 | >100 | >100 | >100 | 20.05 | >100 | >100 | 12.32 |
| 48 | SNU398 | >100 | >100 | >100 | 1.64 | >100 | >100 | 1.91 |
| 49 | SNU423 | >100 | >100 | >100 | 15.32 | >100 | >100 | 9.24 |
| 50 | SNU449 | >100 | >100 | >100 | 13.87 | >100 | >100 | 10.19 |
| 51 | SNU475 | >100 | >100 | >100 | 4.39 | >100 | >100 | 5.37 |
| 52 | SNU739 | >100 | >100 | >100 | 5.29 | >100 | >100 | 5.45 |
| 53 | SNU761 | >100 | >100 | >100 | 8.73 | >100 | >100 | 8.98 |
| 54 | SNU886 | 75.18 | >100 | >100 | 6.19 | >100 | 41.86 | 4.48 |

Note:
The cell lines 29-54 in the table indicates the response of liver cancer cell line to each compound.

As can be seen from the results of Tables 1 and 2, the IC50 values of compounds 1-3 and 10 are close to those of Linifanib in almost all tumor cell lines, while the other 8 compounds (compounds 4-9, 11, and 12) successfully blocked the activity of Linifanib in inhibiting tumor cell proliferation, and the difference in IC50 values between these 8 compounds and the Linifanib is more than 5 times in most tumor cells. There are 3 strains sensitive to Linifanib, KASUMI-1 (leukemia cells), NCI-H1703 (lung cancer cells) and AN3-CA (endometrial cells), with IC50 values of 0.01, 0.02 and 0.19 μM, respectively. The IC50 values for the precursor Linifanib-C12-AA5 (compound 8) were 0.39, 0.19 and 5.68 μM, respectively, with a difference of 39, 8.5 and 29.9 times, respectively.

Among the 54 commercial tumor cell lines, 26 were liver cancer cell lines, and nearly half of the liver cancer cell lines (12/26, 46%) were moderately sensitive to Linifanib, IC50<5 μM, and at the same time for most of the liver cancer cell lines (23/26, 88%), the IC50 values of precursor Linifanib-C12-AA5 (compound 8) were more than 8 times different than the IC50 values of Linifanib, and almost all liver cancer cells did not respond to the intermediates (compound 12), as shown Tables 1 and 2.

Example 45 Plasma Stability Study

The purpose of this example was to investigate the stability of incubation of compound 8 in rat plasma (compound 8 was metabolized to form intermediate compound 12 and Linifanib, intermediate compound 12 was further metabolized to form Linifanib), and the metabolites were quantified and analyzed, and the stability of the incubation system was verified by a positive drug, which provided a reference for the evaluation of the drug-forming properties of the compound.

1. Instruments and Materials
Instrument: API3000 LC/MS, ABI
Materials: Male SD rats (200-250 g), Beijing Vital River
Test sample: positive drug and its metabolites M1 and M2, compound 8 and its metabolite compound 12 and Linifanib.
2. Compound 8 Plasma Stability Study
Test animal
Type: SD rat; Quantity: 2
Sex: male; weight: 200-250 g;

Experimental Procedure
1). Animal blood was collected, blood samples were placed in EDTA anticoagulation tubes, centrifuged at 3000 g for 15 min at 4° C., plasma was separated, and 2 blood samples were mixed in equal volumes;
2). Weighed a certain amount of compound 8 and dissolved in DMSO:MeOH (2:8), prepared into 200 μM mother liquor by purity conversion, and added the compound to plasma to reach a final concentration of 1 μg/mL in plasma. The organic ratio in the system was not more than 0.5%.
3). Incubated in a 37° C. water bath and set the sampling points to 0, 0.5, 1, 2, 4, 6, 8 h. At each sampling point, 100 μL of each sample was collected and 300 μL of acetonitrile (with internal standard) was added for precipitation, centrifuged at 12,000 rpm for 5 min, and 200 μL of supernatant was taken for analysis by LC-MS/MS.
4). Configured the standard curve to quantify compound 8, compound 12 and Linifanib Plasma Stability Study Results
Positive drugs were metabolized in plasma to their metabolites over time as expected, indicating that the plasma system was stable and the subsequent test results are reliable. The plasma stability results of the test compound 8 are shown in Table 3.

As can be seen from Table 3, Compound 8 was relatively stable in plasma, and the amount of Intermediate Compound 12 and Linifanib produced was small, and the peak molar concentration was only $\frac{1}{100}$ and $\frac{1}{1000}$ of Compound 8.

TABLE 3

Experimental results of stability study of compound 8 in rat plasma

| concentration | Residual compound 8 | | Compound 12 produced by compound 8 | | Linifanib produced by compound 8 | |
|---|---|---|---|---|---|---|
| ng/ml | Repeat 1 | Repeat 2 | Repeat 1 | Repeat 2 | Repeat 1 | Repeat 2 |
| 0 h | 1200 | 680 | 0.50 | 0.48 | 0 | 0 |
| 0.5 h | 1190 | 1450 | 8.08 | 9.37 | 0 | 0 |
| 1 h | 1460 | 1620 | 10.8 | 10.6 | 0 | 0 |

TABLE 3-continued

Experimental results of stability study of compound 8 in rat plasma

| concentration | Residual compound 8 | | Compound 12 produced by compound 8 | | Linifanib produced by compound 8 | |
|---|---|---|---|---|---|---|
| ng/ml | Repeat 1 | Repeat 2 | Repeat 1 | Repeat 2 | Repeat 1 | Repeat 2 |
| 2 h | 960 | 1040 | 9.00 | 9.06 | 0.13 | 0.26 |
| 4 h | 876 | 868 | 4.45 | 4.28 | 0.87 | 0.92 |
| 6 h | 1110 | 1190 | 11.1 | 10.7 | 0.60 | 0.74 |
| 8 h | 1200 | 680 | 0.50 | 0.48 | 7.39 | 6.18 |

The above results of the plasma stability study indicate that the stability of Compound 8 in plasma is very good, and the amount of Compound 12 and Linifanib produced by metabolism is extremely small.

The invention claimed is:

1. A pharmaceutical composition comprising a compound having the structure of Formula I, a pharmaceutically acceptable salt or stereoisomer thereof, and a pharmaceutically acceptable carrier,

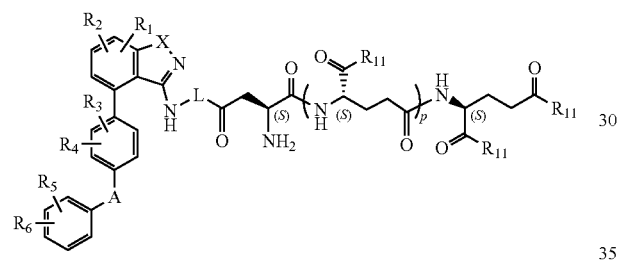

Formula I wherein,

X is $NR_9$;

A is selected from $-N(R_7)C(O)N(R_8)-$ or;

L is $-CO-(CH_2)_n-NH-$, wherein n is 1-11 and p is 0-8;

$R_1$ and $R_2$ are independently selected from the group consisting of hydrogen, alkoxy and alkyl;

$R_3$ and $R_4$ are independently selected from the group consisting of hydrogen, alkoxy, alkyl, halo, haloalkoxy, haloalkyl and hydroxy;

$R_5$ and $R_6$ are independently selected from the group consisting of hydrogen, alkoxy, alkoxyalkyl, alkoxycarbonyl, alkyl, aryloxy, arylalkyl, carboxy, cyano, halo, haloalkoxy, haloalkyl, Hydroxy, hydroxyalkyl, nitro and $-NR_cR_d$;

$R_7$ and $R_8$ are independently selected from the group consisting of hydrogen and alkyl;

$R_9$ is selected from the group consisting of hydrogen, alkenyl, alkoxyalkyl, alkyl, alkoxycarbonyl, aryl, heterocyclylalkyl, hydroxyalkyl and $(NR_aR_b)$alkyl;

$R_{10}$ is selected from the group consisting of hydrogen, alkyl, alkoxy, aryloxy, alkenyloxy, nitro, halo, primary, secondary and tertiary amine;

$R_{11}$ is hydrogen;

$R_a$ and $R_b$ are independently selected from the group consisting of hydrogen, alkyl, alkylcarbonyl, alkyl sulfonyl, aryl sulfonyl, haloalkylsulfonyl and heterocyclylsulfonyl; and, $R_c$ and $R_d$ are independently selected from the group consisting of hydrogen, alkyl, alkylcarbonyl, aryl, arylalkyl, cycloalkyl, cycloalkylalkyl, heterocyclyl and heterocyclylalkyl.

2. A pharmaceutical composition comprising:

a compound, a pharmaceutically acceptable salt or stereoisomer thereof, and a pharmaceutically acceptable carrier;

wherein said compound is selected from the following compounds,

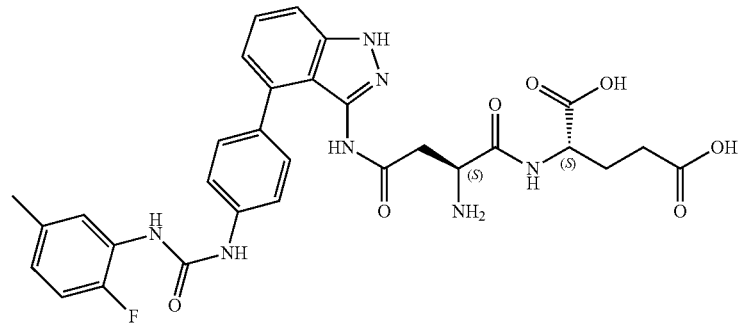

or

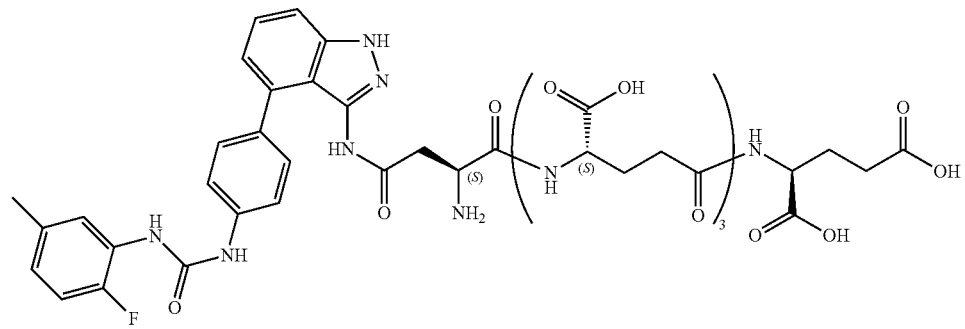

or

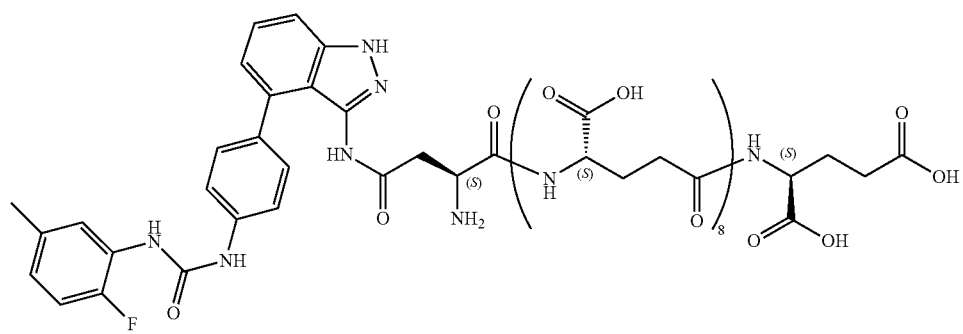
or
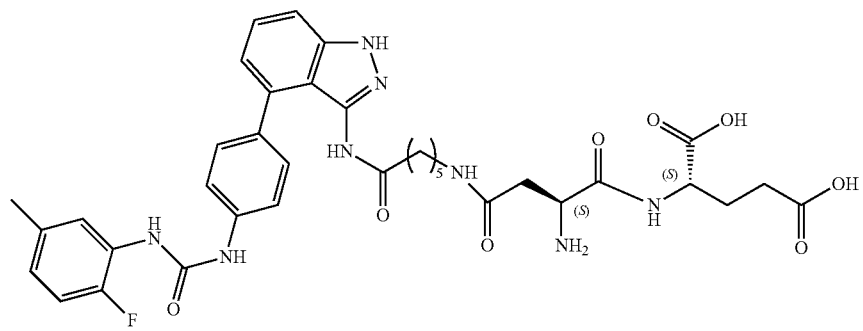
or
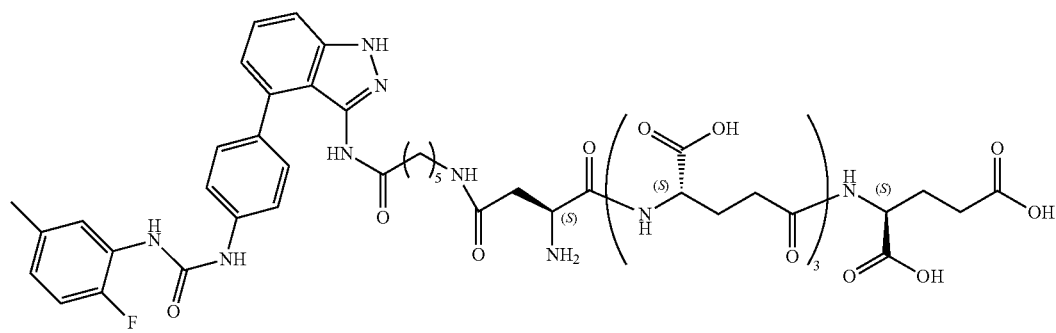
or
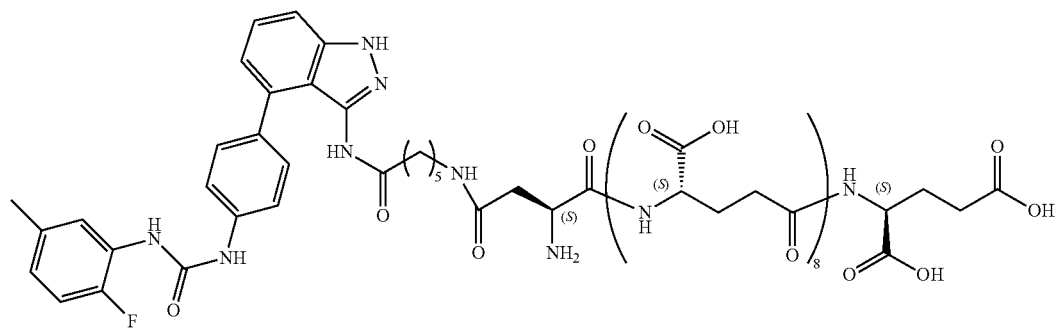
or
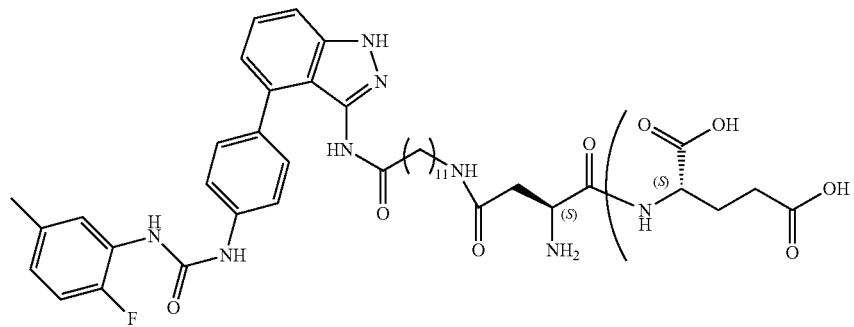
or

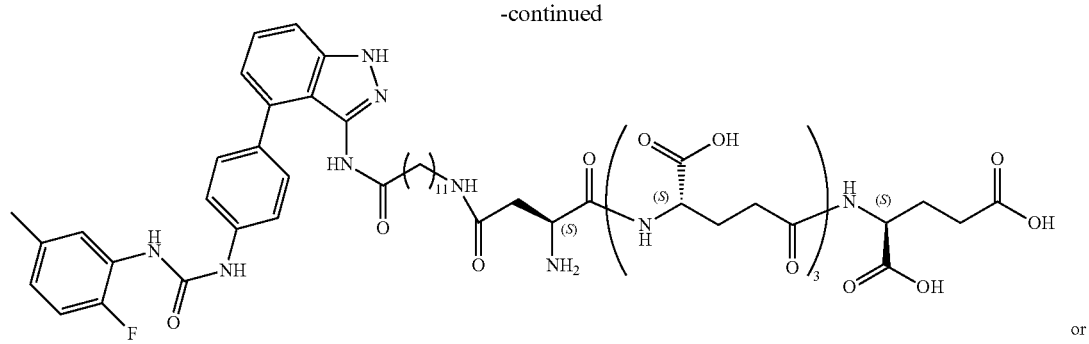
or
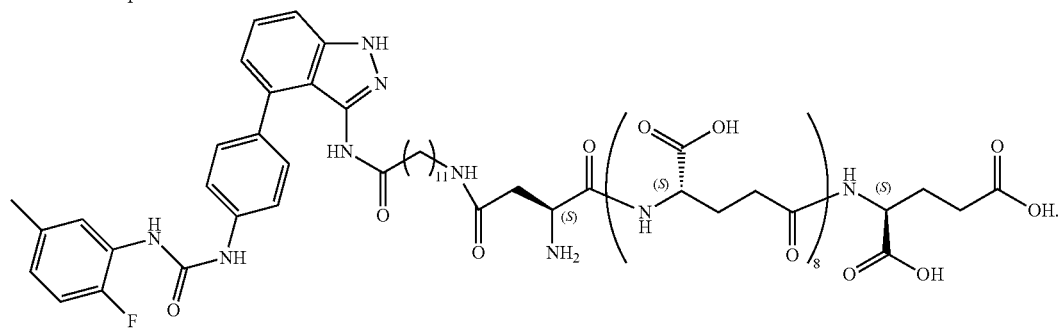
3. A method for preparing the pharmaceutical composition of claim 1 or 2 comprising the following steps:
Step (a), reactant 1, is reacted with reactant 2, with a catalyst and a condensing agent present to obtain a protecting group-containing intermediate compound 1;
Reactant 1
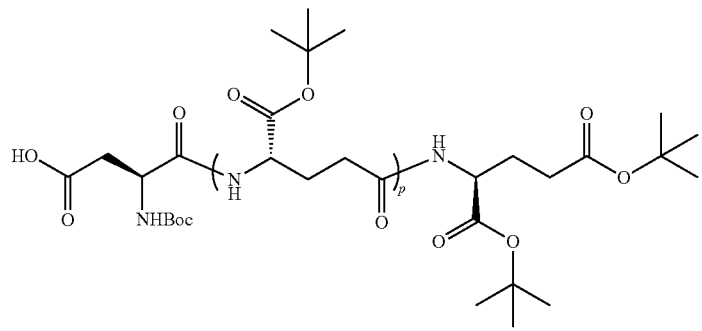
Reactant 2
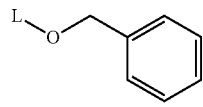
Intermediate compound 1
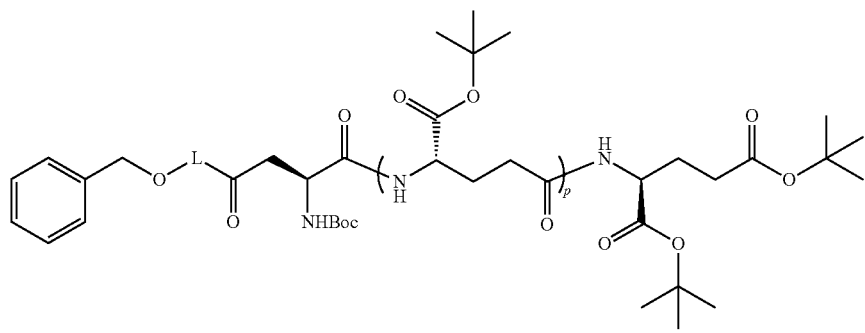

Step (b), the intermediate compound 1 is subjected to catalytic hydrogenation in a polar solvent to remove the protecting group to obtain an intermediate compound 2;

Intermediate compound 2

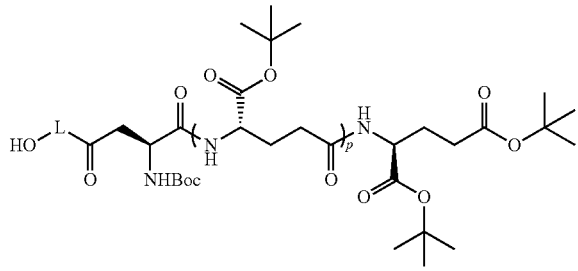

Step (c), the intermediate compound 2 and Linifanib or its derivative are reacted with a catalyst and a condensing agent present to obtain a protecting group-containing intermediate compound 3; and, Step (d), the intermediate compound 3 is subjected to acidic conditions to remove the protecting group to obtain a compound of Formula I;

wherein said catalyst in step (a) is 1-hydroxybenzotriazole; said condensing agent in step (a) is any one or more agents selected from 1-ethyl-3-(3-dimethylaminopropyl)carbodiimide hydrochloride, 1,3-dicyclohexylcarbodiimide or 4-dimethylaminopyridine;

said catalyst in step (b) is palladium on carbon, palladium hydroxide, dry or wet;

said catalyst in step (c) is 1-hydroxybenzotriazole; said condensing agent in step (c) is any one or more agents selected from ethyl-3-(3-dimethylaminopropyl)carbodiimide hydrochloride, 1,3-dicyclohexylcarbodiimide or 4-dimethylaminopyridine;

said acidic reagent in step (d) is formic acid, acetic acid, or trifluoroacetic acid.

4. The method according to claim 3, wherein said step (a) is carried out at a reaction temperature of −20° C. to 125° C.

5. The method according to claim 3, wherein said step (b) is carried out at a reaction temperature of −20° C. to 125° C.

6. The method according to claim 3, wherein said step (c) is carried out at a reaction temperature of −20° C. to 125° C.

7. The method according to claim 3, wherein said step (d) is carried out at a reaction temperature of −20° C. to 125° C.

8. A method for treating a cancer in a subject, said method comprising:
administering to the subject in need thereof the pharmaceutical composition according to claim 1 or 2; said cancer is selected from: endometrial cancer, leukemia, colon cancer, breast cancer, liver cancer, lung cancer, prostate cancer, and renal cancer.

9. A method for treating liver cancer in a subject, said method comprising:
administering to the subject in need thereof the pharmaceutical composition according to claim 1 or 2.

Intermediate compound 3

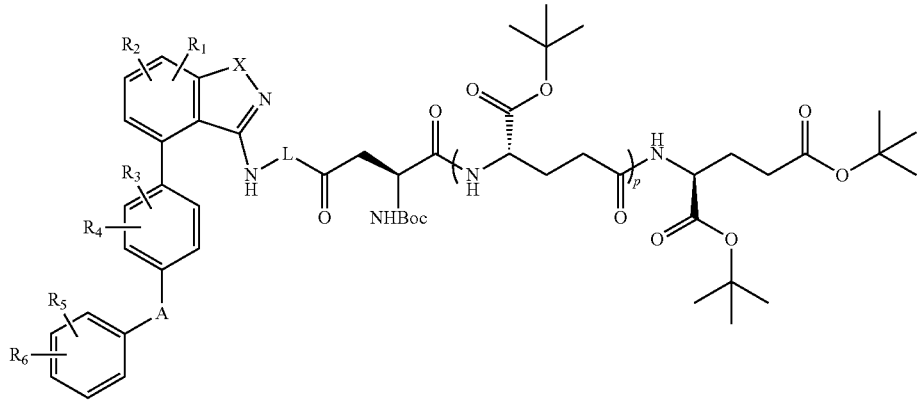

* * * * *